United States Patent
Wang et al.

(10) Patent No.: US 10,780,116 B2
(45) Date of Patent: Sep. 22, 2020

(54) USE OF FULLERENE STRUCTURE IN PREPARATION OF MEDICAMENTS FOR TREATING PARKINSON'S DISEASE

(71) Applicant: Beijing Fullcan Biotechnology Co., LTD, Beijing (CN)

(72) Inventors: Chunru Wang, Beijing (CN); Mingming Zhen, Beijing (CN); Xue Li, Beijing (CN); Hui Li, Beijing (CN); Xuekai Bai, Beijing (CN); Chunli Bai, Beijing (CN)

(73) Assignee: BEIJING FULLCAN BIOTECHNOLOGY CO., LTD, Beijing (CN)

( * ) Notice: Subject to any disclaimer, the term of this patent is extended or adjusted under 35 U.S.C. 154(b) by 0 days.

(21) Appl. No.: 16/074,584

(22) PCT Filed: Mar. 31, 2017

(86) PCT No.: PCT/CN2017/078950
§ 371 (c)(1),
(2) Date: Aug. 1, 2018

(87) PCT Pub. No.: WO2017/133714
PCT Pub. Date: Aug. 10, 2017

(65) Prior Publication Data
US 2019/0038668 A1    Feb. 7, 2019

(30) Foreign Application Priority Data
Feb. 1, 2016    (CN) .......................... 2016 1 0069258

(51) Int. Cl.
*A61K 33/44*    (2006.01)
*C01B 32/152*    (2017.01)
(Continued)

(52) U.S. Cl.
CPC .............. *A61K 33/44* (2013.01); *A61K 9/08* (2013.01); *A61K 9/10* (2013.01); *A61K 9/145* (2013.01);
(Continued)

(58) Field of Classification Search
None
See application file for complete search history.

(56) References Cited

U.S. PATENT DOCUMENTS

2005/0130939 A1*  6/2005  Wilson ................. A61K 8/19
                                                            514/79
2008/0206222 A1*  8/2008  Miwa .................. A61K 8/19
                                                            424/94.6

FOREIGN PATENT DOCUMENTS

CN    101098684    1/2008
CN    101475520    7/2009
(Continued)

OTHER PUBLICATIONS

Light, "C60 Olive oil miracle health product?", Hyberborean Health, pp. 1-12, 2014 (Year: 2014).*
(Continued)

*Primary Examiner* — Kyung S Chang
(74) *Attorney, Agent, or Firm* — Hauptman Ham, LLP

(57) ABSTRACT

An application of a fullerene structure in the preparation of medications for treating Parkinson's disease. The fullerene structure comprises at least one of the following active ingredient groups: a fullerene, a metallofullerene, and a composition of the fullerene and the metallofullerene; an oil-soluble fullerene, an oil-soluble metallofullerene, and a composition of the oil-soluble fullerene and the oil-soluble metallofullerene; a water-soluble fullerene, a water-soluble metallofullerene, and a composition of the water-soluble fullerene and the water-soluble metallofullerene; the medici- (Continued)

nal esters of the nine elements, or the medicinal salts of the nine elements.

10 Claims, 15 Drawing Sheets

(51) Int. Cl.

| | |
|---|---|
| *C01B 32/156* | (2017.01) |
| *A61K 47/44* | (2017.01) |
| *A61K 31/015* | (2006.01) |
| *A61K 9/14* | (2006.01) |
| *A61P 39/06* | (2006.01) |
| *A61P 7/00* | (2006.01) |
| *A61P 25/16* | (2006.01) |
| *A61P 9/10* | (2006.01) |
| *B82Y 5/00* | (2011.01) |
| *A61K 9/10* | (2006.01) |
| *A61K 47/40* | (2006.01) |
| *C01B 32/154* | (2017.01) |
| *A61K 9/08* | (2006.01) |

(52) U.S. Cl.
CPC ............ *A61K 31/015* (2013.01); *A61K 47/40* (2013.01); *A61K 47/44* (2013.01); *A61P 25/16* (2018.01); *C01B 32/152* (2017.08); *C01B 32/154* (2017.08); *C01B 32/156* (2017.08)

(56) References Cited

FOREIGN PATENT DOCUMENTS

| | | | |
|---|---|---|---|
| CN | 103826472 | 5/2014 | |
| CN | 104127872 | 11/2014 | |
| CN | 104997646 | 10/2015 | |
| CN | 105596368 | 5/2016 | |
| WO | 2005035441 | 4/2005 | |
| WO | 2012097245 | 7/2012 | |
| WO | WO-2013025180 A1 * | 2/2013 | ............. A23L 33/10 |

OTHER PUBLICATIONS

Gazewood et al., "Parkinson Disease: An Update", American Family Physician, vol. 87, #5, 2013, pp. 267-273 (Year: 2013).*
Yang et al., "[Gd@C82(OH)22]n Nanoparticles Induce Dendritic Cell Maturation and Activate Th1 Immune Responses", ACS Publications, 2010, 4, 2, p. 1178-1186 (Year: 2010).*
International search report dated Jul. 3, 2017 from corresponding application No. PCT/CN2017/078950.
Office Action dated Dec. 29, 2017 and English translation from corresponding application No. CN 201610069258.6.
Xiaoming Li et al., "Biosafety and toxicity of nanoparticles and tubular materials"; Intellectual Property Press, Jul. 31, 2014; p. 11.
Search Report dated Dec. 11, 2017 and English translation from corresponding application No. CN 201610069258.6.
Examination Report dated Dec. 5, 2019 from corresponding application No. AU 2017214167.
Dugan LL, et al. "Carboxyfullerene neuroprotection postinjury in Parkinsonian nonhuman primates", Ann Neurol. 2014;76(3):393-402.
Baati T, et al. "The prolongation of the lifespan of rats by repeated oral administration of [60]fullerene", Biomaterials. Jun. 2012, 33(19), pp. 4936-4946.
Light S, "C60 Olive oil miracle health product?", Hyberboreanhealth.corn [retrieved from Internet on Nov. 25, 2019] < URL: https://hyperboreanhealth.com/c60-olive-oil-miracle-health-product> published on Jul. 19, 2014.
Krusic PJ, et al. "Radical reactions of C60", Science, Nov. 22, 1991;254(5035), pp. 1183-1185.

* cited by examiner

As compared with normal saline control group, ### represents p < 0.001; as compared with modeling group, * represents p < 0.05,  represents p < 0.01, * represents p < 0.001; as compared with olive oil group, △△△ represents p < 0.001

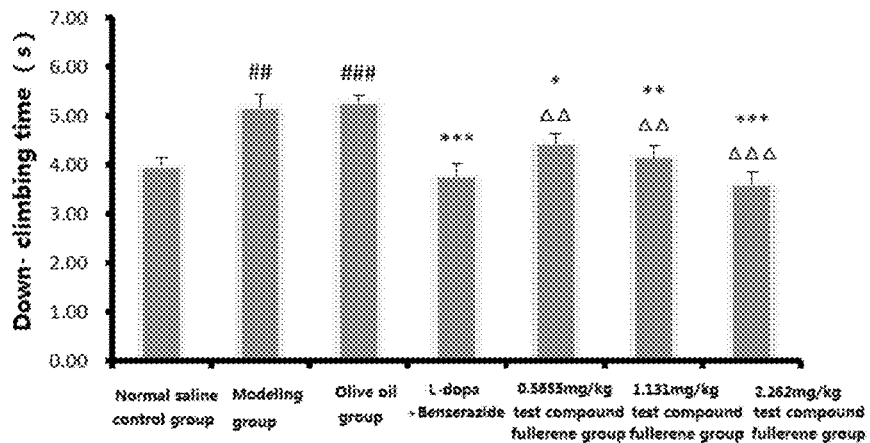

As compared with normal saline group, ## represents p < 0.01, ### represents p < 0.001; as compared with modeling group, * represents p < 0.05,  represents p < 0.01, * represents p < 0.001; as compared with olive oil group, △△ represents p < 0.01, △△△ represents p < 0.001

Fig. 20

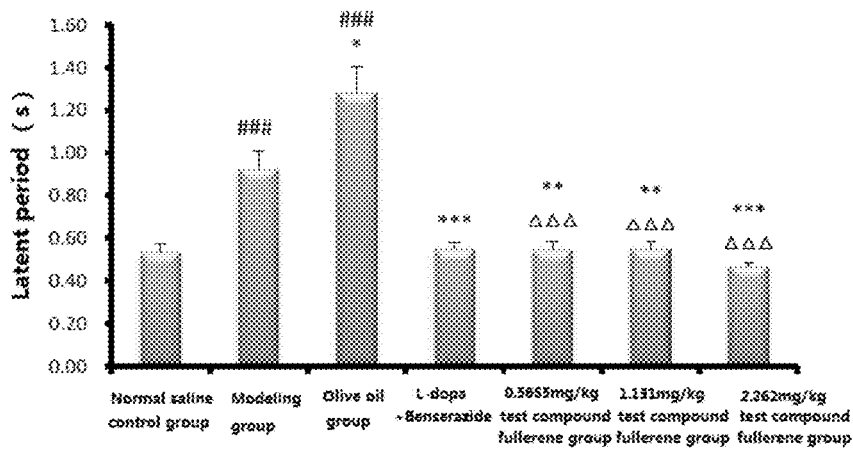

As compared with normal saline control group, ### represents p < 0.001; as compared with modeling group, * represents p < 0.05,  represents p < 0.01, * represents p < 0.001; as compared with olive oil group, △△△ represents p < 0.001

Fig. 21

As compared with normal saline group, # represents p < 0.05, ## represents p < 0.01; as compared with modeling group, ** represents p < 0.01; as compared with olive oil group, △△△ represents p < 0.001

As compared with normal saline control group, ### represents p < 0.001; as compared with modeling group, * represents p < 0.05, *** represents p < 0.001; as compared with olive oil group, △ represents p < 0.05, △△ represents p < 0.01

As compared with normal saline control group, # represents p < 0.05, ## represents p < 0.01; as compared with modeling group, * represents p < 0.05; as compared with olive oil group, △ represents p < 0.05

As compared with normal saline control group, # represents p < 0.05, ## represents p < 0.01; as compared with modeling group, * represents p < 0.05

As compared with normal saline control group, ## represents p < 0.01 ; as compared with modeling group,* represents p < 0.05

As compared with normal saline control group, ## represents p < 0.01 ; as compared with modeling group,* represents p < 0.05; as compared with olive oil group,△ represents p < 0.05

USE OF FULLERENE STRUCTURE IN PREPARATION OF MEDICAMENTS FOR TREATING PARKINSON'S DISEASE

RELATED APPLICATIONS

The present application is a National Phase of International Application Number PCT/CN2017/078950, filed Mar. 31, 2017, and claims the priority of China Application No. 201610069258.6, filed Feb. 1, 2016.

FIELD OF THE INVENTION

The disclosure belongs to the field of biomedicine and particularly relates to a use of a fullerene structure in preparation of a medicament for treating Parkinson's disease.

BACKGROUND ART

Parkinson's disease (PD) is a common degenerative disease of the central nervous system characterized by the degeneration of the nigrostriatal pathway, which occurs most frequently in the elderly people and an average onset age of which is about 60 years. The pathologic change of PD is mainly the degeneration death of dopaminergic neurons in the midbrain substantia nigra, which leads to diseases due to a significant reduction in the content of the striatal dopamine. The clinical manifestations of PD are mainly static tremors, bradykinesia, myotonia and posture gait disorders. According to the survey, the incidence rate of Parkinson's disease at the age of 65 or older reaches 1-2%. With the aging of the population, the study on Parkinson's disease has gradually gained people's attention. The pathogenesis of Parkinson's disease is still unknown. Ageing, genetic factors, environmental factors, and oxidative stress are all possibly related to Parkinson's disease. At present, most scholars agree more on the doctrine of the mitochondrial dysfunction andoxidative stress, namely the inhibition of mitochondrial I complexes leads to a large number of free radicals, a large number of free radicals are also produced by the oxidative stress, which correspondingly reduces the activity of the mitochondrial I complexes, thereby increasing the toxicity to the neurons. However, there is no good treatment approach for Parkinson's disease at present, instead, medication treatment is still a primary method for the treatment.

Fullerenes are another allotrope of carbon besides graphite, diamond, and amorphous carbon. This kind of substance refers to a cage-like structure composed of carbon atoms, the largest amount of the molecule of fullerenes is $C_{60}$, followed by $C_{70}$ and $C_{84}$, while the relatively small amount of the molecule is $C_{76}$, followed by $C_{78}$ and $C_{80}$. In addition, due to the hollow structure of the carbon cage of the fullerene, the internal cavity of the fullerene embedded with different atoms, ions, or clusters are called endohedral fullerenes, such as La@$C_{60}$, meaning that La is embedded in the cage structure of $C_{60}$, @ represents at, and vividly means embedding.

The information disclosed in this background art is only for enhancement of understanding of the general background of the present invention and should not be taken as an acknowledgement or any form of suggestion that this information has already been part of the prior art known to those skilled in the art.

SUMMARY OF THE INVENTION

An object of the present disclosure includes providing a use of a fullerene structure in the preparation of a medicament for treating Parkinson's disease, and the object of the present disclosure also includes providing a pharmaceutical composition and method for treating Parkinson's disease. According to the free radicals-scavenging effect and monodispersity of the fullerene structure of the present disclosure, Parkinson's disease can be treated through the blood-brain barrier, and physical disabilities and dyskinesia caused by Parkinson's disease can indeed be treated, which proves that the fullerene structure of the active ingredient of the present disclosure has significant efficacy in treating Parkinson's disease, and can improve the quality of patients' life.

In order to achieve the object, the present disclosure provides the following technical solutions: A use of a fullerene structure in the preparation of a medicament for treating Parkinson's disease, wherein the fullerene structure comprises at least one effective ingredient selected from the group consisting of a fullerene body, a metallofullerene body, and a composition of the fullerene body and the metallofullerene body; an oil-soluble fullerene, an oil-soluble metallofullerene, and a composition of the oil-soluble fullerene and the oil-soluble metallofullerene; a water-soluble fullerene, a water-soluble metallofullerene, and a composition of the water-soluble fullerene and the water-soluble metallofullerene; and pharmaceutically-acceptable esters or salts of the above nine ingredients.

The present disclosure also provides a method for treating Parkinson's disease comprising the steps of administering an effective dose of a fullerene structure to a subject in need of treatment for Parkinson's disease, wherein the fullerene structure comprises at least one effective ingredient selected from the group consisting of a fullerene body, a metallofullerene body, and a composition of the fullerene body and the metallofullerene body; an oil-soluble fullerene, an oil-soluble metallofullerene, and a composition of the oil-soluble fullerene and the oil-soluble metallofullerene; a water-soluble fullerene, a water-soluble metallofullerene, and a composition of the water-soluble fullerene and the water-soluble metallofullerene; and pharmaceutically-acceptable esters or salts of the above nine ingredients.

The present disclosure also provides a pharmaceutical composition for treating Parkinson's disease, comprising a fullerene structure, further comprising at least one of a pharmaceutically-acceptable carrier, a pharmaceutically-acceptable diluent and a pharmaceutically-acceptable excipient, wherein the fullerene structure comprises at least one effective ingredient selected from the group consisting of a fullerene body, a metallofullerene body, and a composition of the fullerene body and the metallofullerene body; an oil-soluble fullerene, an oil-soluble metallofullerene, and a composition of the oil-soluble fullerene and the oil-soluble metallofullerene; a water-soluble fullerene, a water-soluble metallofullerene, and a composition of the water-soluble fullerene and the water-soluble metallofullerene; and pharmaceutically-acceptable esters or salts of the above nine ingredients.

According to the above use, method or pharmaceutical composition in another embodiment, the oil-soluble fullerene comprises a fullerene with the outer surface of the carbon cage being coated with an oil solution; the oil-soluble metallofullerene includes a metallofullerene with the outer surface of the carbon cage being coated with an oil solution.

According to the above uses, methods or pharmaceutical compositions in another embodiment, the oil solution may be a single ingredient oil or a mixture of different oils, which are usually vegetable oils such as olive oil, linseed oil, sunflower oil, corn germ oil, soybean oil, etc., as well as animal fats such as squalane, etc.

According to the above uses, methods or pharmaceutical compositions in another embodiment, the fullerene with the outer surface of the carbon cage being coated with an oil solution is obtained through oil-soluble modification of the fullerene body, and the metallofullerene with outer surface of the carbon cage being coated with an oil solution is obtained through oil-soluble modification of the metallofullerene body.

According to the above uses, methods or pharmaceutical compositions in another embodiment, the oil-soluble modification is to disperse at least one of a fullerene body and a metallofullerene body in the oil solution to obtain an oil-soluble modified liquid; the specific steps of dispersion may be ball milling or ultrasonication of the mixture of the body and the oil solution, followed by centrifugation to remove the precipitate, and filtration of the resulting supernatant. Fullerenes and/or metallofullerenes can be present in a monodisperse form by means of ball milling or ultrasonication; monodispersed fullerenes and/or metallofullerenes can enter the brain tissue through the blood-brain barrier.

According to the above uses, methods or pharmaceutical compositions in another embodiment, the concentration of the effective ingredient in the oil-soluble modified liquid is from 0.01 to 100 mg/mL, and the disclosure of this range should be regarded as disclosure of all numerical values within the range, optionally from 0.01 to 10 mg/mL, from 10 to 20 mg/mL, from 20 to 30 mg/mL, from 30 to 40 mg/mL, from 0.01 to 0.8 mg/mL, and from 0.4 to 0.8 mg/mL, etc.

According to the above uses, methods or pharmaceutical compositions in another embodiment, during the oil-soluble modification, from 0.05 to 1000 mg of a fullerene body and/or a metallofullerene body are dispersed per 1 ml of the oil solution. The disclosure of the range should be considered as disclosure of all numerical values within the range, optionally from 0.05 to 1 mg, from 0.05 to 10 mg, and from 0.05 to 100 mg, etc.

According to the above uses, methods or pharmaceutical compositions in another embodiment, the mixture of the body and the oil solution is carried out ball milling or ultrasonication for 30 minutes to 15 hours.

According to the above uses, methods or pharmaceutical compositions in another embodiment, in the oil-soluble modified liquid, the particle size of the fullerene or the metallofullerene may be from 0.7 nm to 1 nm.

According to the above uses, methods or pharmaceutical compositions in another embodiment, after the mixture of the body and the oil solution is carried out ball milling or ultrasonication and before centrifugation, the method further comprises the step of keeping the mixture in a cool, dry, dark place for storage for a certain period of time. Optionally, the certain period of time refers to 2 h to 24 h.

According to the above uses, methods or pharmaceutical compositions in another embodiment, the water-soluble fullerene includes one or more selected from the group consisting of: (1) a fullerene with the outer surface of the carbon cage being modified with a hydrophilic group; (2) a fullerene with the outer surface of the carbon cage being wrapped by a hydrophilic small biological molecule; (3) a fullerene supported by a carrier material having biocompatibility; (4) self-assembled water-soluble supramolecular system of fullerene.

According to the above uses, methods or pharmaceutical compositions in another embodiment, the water-soluble metallofullerene includes one or more selected from the group consisting of: (1) a metallofullerene with the outer surface of the carbon cage being modified with a hydrophilic group; (2) a metallofullerene with the outer surface of the carbon cage being wrapped by a hydrophilic small biological molecule; (3) a metallofullerene supported by a carrier material having biocompatibility; (4) self-assembled water-soluble supramolecular system of metallofullerene.

According to the above uses, methods or pharmaceutical compositions in another embodiment, the hydrophilic group includes one or more of a hydroxyl group, a carboxyl group, a sulfhydryl group, and an amino group.

According to the above uses, methods or pharmaceutical compositions in another embodiment, the water-soluble metallofullerene includes water-soluble hydroxylated $Gd@C_{82}$; the water-soluble fullerene includes water-soluble hydroxylated $C_{60}$ or water-soluble hydroxylated $C_{70}$.

According to the above uses, methods or pharmaceutical compositions in another embodiment, the hydrophilic small biological molecule include at least one of an amino acid and a peptide chain According to the above uses, methods or pharmaceutical compositions in another embodiment, the carrier material having biocompatible includes at least one of a liposome and a cell membrane carrier.

According to the above uses, methods or pharmaceutical compositions in another embodiment, the biocompatible carrier material is a pharmaceutical carrier commonly used in medicine, including at least one of a liposome and a cell membrane carrier. Optionally, the polymer micelle is poly-lactide-co-glycolide-co-poly(ethylene glycol) (PEG-PLGA), polylysine or chitosan; and the protein is albumin or transferrin.

According to the above uses, methods or pharmaceutical compositions in another embodiment, the water-soluble fullerene is obtained by water-soluble modification of a fullerene body; and the water-soluble metallofullerene is obtained by water-soluble modification of a metallofullerene body.

According to the above uses, methods or pharmaceutical compositions in another embodiment, the method of water-soluble modification is any one of the following methods: (1) the method of surface modification of a hydrophilic group is generally realized by a solid-liquid or liquid-liquid reaction under the action of a base. Specifically, at least one of a fullerene body and a metallofullerene body is mixed and reacted with hydrogen peroxide and a base (specifically, the base can be sodium hydroxide or potassium hydroxide), the mixture is washed with ethanol and then dialyzed to obtain the water-soluble hydroxyl derivatives corresponding to the body. If it is necessary to obtain a water-soluble aminated derivative, the hydroxide in the above step may be replaced with ammonia. (2) A method of physical coating may comprise the following steps: at least one of a fullerene body and an metallofullerene body is mixed with at least one of polyethylene glycol, polyvinylpyrrolidone, and cyclodextrin and is then carried out ball milling or ultrasonication to obtain the coated water-soluble fullerene structure corresponding to the body, such as a polyethylene glycol-coated fullerene and/or a polyethylene glycol-coated metallofullerene, a polyvinyl pyrrolidone-coated fullerene and/or a polyvinyl pyrrolidone-coated metallofullerene.

According to the above uses, methods or pharmaceutical compositions in another embodiment, from 50 to 300 mg of $C_{60}$ or $C_{70}$ or $Gd@C_{82}$ solid are weighed and mixed with from 5 to 30 ml of 20 to 40% hydrogen peroxide and from 2 to 20 ml of 1 M to 3 M alkaline solution, at 50 to 100° C. until all solids of $C_{60}$ or $C_{70}$ or $Gd@C_{82}$ are dissolved. In this description, the proportional relationship among the substances is represented, and the reaction scale is not limited by the specific reaction scales of from 50 to 300 mg, from 5 to 30 ml, and from 2 to 20 ml in the practical applications, and can be expanded in proportion.

According to the above uses, methods or pharmaceutical compositions in another embodiment, the fullerene body comprises one or more cage-like structures consisting of carbon atoms with a general formula $C_{2m}$, $30 \leq m \leq 60$, for example, $C_{60}$, $C_{70}$ and $C_{84}$, etc.

According to the above uses, methods or pharmaceutical compositions in another embodiment, the metallofullerene body comprises one or more of $M@C_{2n}$, $M_2@C_{2n}$, $MA@C_{2n}$, $M_3N@C_{2n}$, $M_2C_2@C_{2n}$, $M_2S@C_{2n}$, $M_2O@C_{2n}$ and $M_xA_{3-x}N@C_{2n}$, wherein each of M and A represents a metal element, and M, A are all selected from any one of a lanthanoid metal element, Sc, and Y, $30 \leq n \leq 60$; $0 \leq x \leq 3$. N represents a nitrogen element, C represents a carbon element, S represents a sulfur element, and lanthanoid metal elements include La, Ce, Pr, Nd, Pm, Sm, Eu, Gd, Tb, Dy, Ho, Er, Tm, Yb and Lu. For example: $Gd@C_{82}$.

According to the above uses, methods or pharmaceutical compositions in another embodiment, the Parkinson's disease includes physical disabilities and dyskinesia caused by Parkinson's disease including, but not limited to, limbs tremor, rigid limbs, hypokinesia, bradykinesia, or discordant movement.

According to the above uses, methods or pharmaceutical compositions in another embodiment, the Parkinson's disease is caused by a neurotoxin, including but not limited to 1-methyl-4-phenyl-1,2,3,6-tetrahydropyridine or a salt thereof that can be absorbed by a subject, such as 1-methyl-4-phenyl-1,2,3,6-tetrahydropyridine hydrochloride.

According to the medicament in the above uses or the above pharmaceutical compositions in another embodiment, the medicament or pharmaceutical composition may be formulations such as tablets, pills, powders, lozenges, sachets, cachets, elixirs, suspensions, emulsions, solutions, syrups, aerosols, ointments, soft and hard gelatine capsules, suppositories, sterile injectable solutions or sterile packaged powder-injections. The method for preparing the effective ingredient as a medicament or a pharmaceutical composition in the present disclosure can be a method well known to those skilled in the art, so that the effective ingredient can be released immediately, slowly released or delayed to be released after being administered to a subject, for example: the effective ingredient may be mixed with the carrier, diluted with the carrier or encapsulated in the carrier.

The medicaments in the above uses or the above pharmaceutical compositions in another embodiment, some examples suitable as the carriers, excipients, and diluents include lactose, dextrose, sucrose, sorbitol, mannitol, starch, resins, gum arabic, calcium phosphate, alginate, tragacanth, gelatin, calcium silicate, microcrystalline cellulose, polyvinyl pyrrolidone, cellulose, water syrup, methyl cellulose, methyl paraben and propyl paraben, talcum powder, magnesium stearate and liquid paraffin.

According to the medicaments in the above uses or the above pharmaceutical compositions in another embodiment, the medicament or pharmaceutical composition may further include a lubricant, a wetting agent, an emulsifying and suspending agent, a preservative, a sweetening agent, or a flavoring agent, etc.

According to the above method in another embodiment, the subject is a human or an animal, and the animal may be a mammal, such as a mouse, a guinea pig, a rat, a dog, a rabbit and a monkey, etc.

According to the above methods in another embodiment, the effective ingredient is applied at a dose of from 0.01 mg/kg/d to 1000 mg/kg/d. The disclosure of this range should be regarded as disclosure of all numerical values within the range, optionally from 1 to 100 mg/kg/d, from 10 mg/kg/d to 100 mg/kg/d, from 1 to 20 mg/kg/d, from 0.1 to 10 mg/kg/d, or 4 mg/kg/d. The course of administration may be from 5 days to 30 days, such as: 15 days, the administration can be short-term or long-term according to the condition of the subject; the effective ingredients can be administered orally, by injection (e.g. intravenous injection) or intraperitoneally. After the injection, the effective ingredients enter the body and exert their effect directly through the blood circulation without penetration. The dose of the medicament used is small and the curative effect is high. Oral administration functions by being filtered and absorbed through the digestive system, with less side effects but a significant effect.

According to the medicaments in the above uses or the above pharmaceutical compositions in another embodiment, when the medicament or the pharmaceutical composition is in liquid form, the concentration of the effective ingredient in the medicament or the pharmaceutical composition is from 0.01 to 100 mg/mL, optionally from 0.01 to 10 mg/mL, from 0.01 to 20 mg/mL, from 0.01 to 30 mg/mL, and from 0.01 to 40 mg/mL; when the medicament or the pharmaceutical composition is present in form of solid, the concentration of the effective ingredients in the medicament or the pharmaceutical composition is from 0.01 to 50 mg/g, optionally from 0.01 to 10 mg/g, from 0.01 to 20 mg/g, from 0.01 to 30 mg/g, and from 0.01 to 40 mg/g.

According to the medicaments in the above uses or the above pharmaceutical compositions in another embodiment, the concentration of the water-soluble fullerene and/or water-soluble metallofullerene in the preparation is from 0.01 to 100 mg/mL; the concentration of the oil-soluble fullerene and/or oil-soluble metallofullerene in the formulation is from 500 ppm to 10000 ppm (mg/kg).

The term "treat" or "treating" used herein includes its generally-accepted meanings including stopping, preventing, inhibiting, improving, alleviating, arresting, or reversing the development of symptom or the development of a desired disease. As such, the present disclosure encompasses both therapeutic and prophylactic administration.

The terms "effective ingredient", "effective ingredient fullerene structure" or "fullerene structure" used herein all refer to at least one of a fullerene body, a metallofullerene body, a composition of the fullerene body and the metallofullerene body; an oil-soluble fullerene, an oil-soluble metallofullerene, and a composition of the oil-soluble fullerene and the oil-soluble metallofullerene; a water-soluble fullerene, a water-soluble metallofullerene, and a composition of the water-soluble fullerene and the water-soluble metallofullerene; the pharmaceutically-acceptable esters or salts of the above nine ingredients.

The term "effective dose" or "effective amount" used herein refers to an amount or dose of an effective ingredient that is administered to a patient at a single or multiple times to provide the desired effect to the patient being diagnosed or treated. The effective dose may be determined by the participating diagnostician as those skilled in the art with the known techniques and observed result obtained under similar circumstances. In determining the effective amount or dose of the effective ingredient administered, the participating diagnostician should consider a variety of factors including, but not limited to: mammal species; size, age and average health condition; specific diseases involved; the extent or severity of the disease involved; individual patient response; the specific compound administered; mode of administration; bioavailability properties of the formulation administered; the selected administration regime; use of concomitant medications; and other relevant circumstances.

The term "fullerene body" used herein refers to a fullerene that has not been carried out water-soluble modification or oil-soluble modification.

The term "metallofullerene body" used herein refers to a metallofullerene that has not been carried out water-soluble modification or oil-soluble modification.

In order to facilitate the metering, all restrictions on the specific content, concentration, etc. of water-soluble fullerenes, water-soluble metallofullerenes, oil-soluble fullerenes, or oil-soluble metallofullerenes in the present disclosure are based on their corresponding specific content and concentration of the fullerene body or metallofullerene body. For example, the concentration of the water-soluble fullerene in the formulation is from 0.01 to 100 mg/mL, which means that the concentration of carbon cage of the fullerene body detected in the water-soluble fullerenes in the formulation is from 0.01 to 100 mg/mL; for another example, the content of fullerene coated with the oil solution on the outer surface of the carbon cage is 100 µM, which means that the content of the fullerene body carbon cage in the oil solution is 100 µM. Among them: metallofullerenes can be quantitatively determined by inductively coupled plasma emission spectrometer (ICP). Compared with the prior art, the beneficial effects of the present disclosure include:

1. Good Biocompatibility, Safety and Non-Toxic Side Effects.

After the effective ingredient fullerene structure enters the body, it can be rapidly metabolized, has no obvious cytotoxicity to living body and normal cells, does not cause damage to organs, and it is safe and nontoxic, and has good biocompatibility.

2. Significant Effect.

The effective ingredient fullerene structure maintains the high conjugacy and free radicals scavenging effect of fullerene molecules, etc. It was improved by the ESR test in vitro that the effective ingredient fullerene structure has the strong free radical scavenging effect of fullerene molecules. Then it was proved by cell-level experiments that the effective ingredient fullerene structure had no damage to but can protect the cells and can also repair cell damage caused by free radicals. Finally, it was found to be possible to treat physical disabilities and dyskinesia caused by Parkinson's disease in mice by building a Parkinson mouse model and applying the fullerene structure as an effective ingredient of the present disclosure for treatment, such as limbs tremor, rigid limbs, hypokinesia, bradykinesia, or discordant movement, which proves that the effective ingredient fullerene structure of the present disclosure has significant efficacy in treating Parkinson's disease and can improve the quality of life of patients.

DESCRIPTION OF THE DRAWINGS

FIG. 20 is a graph showing the down-climbing time of mice tested by the pole test after the mice administration of day 6 in Example 6.

FIG. 21 is a graph showing the latent period of mice tested by the pole test after the mice administration of day 9 in Example 6.

DESCRIPTION OF THE PREFERRED EMBODIMENT

Figure 1:
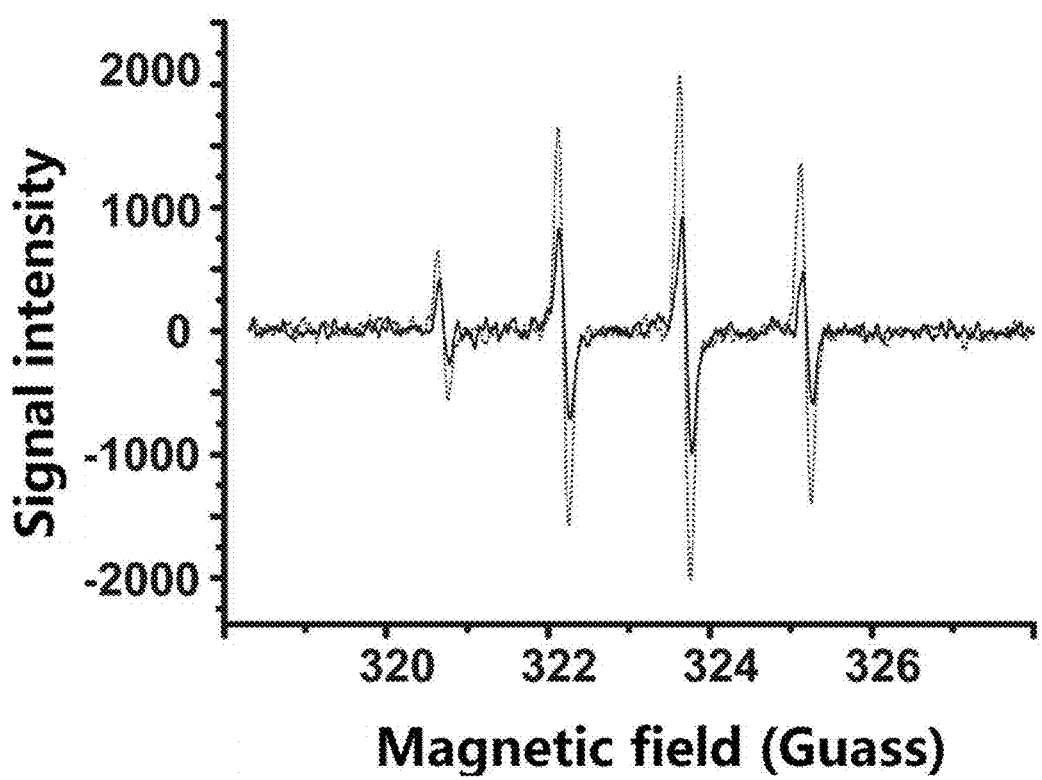
FIG. 1 is an electron spin resonance (ESR) control diagram in which the dashed line is the blank control without Gd@$C_{82}$-olive oil and the solid line is the experimental group having Gd@$C_{82}$-olive oil obtained in Example 1.

The present disclosure will be described below with reference to specific embodiments through the accompanying drawings, but the present disclosure is not limited to the following embodiments.

Solid powders of the fullerene body $C_{60}$ and $C_{70}$ and solid powders of the metallofullerene body $Gd@C_{82}$ with a purity of 99% used in the examples of the present disclosure were all purchased from Xiamen Funano New Material Technology Company LTD. Other materials, reagents, and instruments used can be commercially available unless otherwise specified; other experimental methods are all conventional methods unless otherwise specified.

Example 1. Preparation of Oil-Coated Hollow Fullerenes and/or Oil-Coated Metallofullerenes 20 ml of olive oil was measured, 20 mg of $C_{60}$ or 20 mg of $C_{70}$ or 20 mg of $Gd@C_{82}$ (particle sizes are all 0.7-1 nm) was weighed, and they were mixed and stirred evenly to obtain a mixture; then, the mixture was placed in a ball mill to be ball-milled for 10 hours, after that, the mixture was taken out, stored in a cool, dry and dark place, and left standstill for 1 hour, the precipitate was centrifuged to be removed, and then the resulting supernatant was filtered using a 220 nm filter membrane to get final product. In the present disclosure, the oil-soluble fullerene prepared from the olive oil and $C_{60}$ according to the above method was called $C_{60}$-olive oil for short, wherein the content of the $C_{60}$ was 0.8 mg/mL; the oil-soluble fullerene prepared from the olive oil and $C_{70}$ according to the above method was called $C_{70}$-olive oil for short; the oil-soluble metallofullerene prepared from the olive oil and $Gd@C_{82}$ according to the above method was called $Gd@C_{82}$-olive oil for short, wherein the content of the $Gd@C_{82}$ was 0.4 mg/mL.

Example 2. Preparation of Water-Soluble Hydroxylated Hollow Fullerenes and/or Water-Soluble Hydroxylated Metallofullerenes 1) 100 mg of $Gd@C_{82}$ solid powder or 100 mg of $C_{60}$ solid powder was added to a 100 ml of single-mouth flask, 7 ml of a 30% by volume aqueous hydrogen peroxide solution and 3 ml of a 2M aqueous sodium hydroxide solution were respectively added, and the oil bath was heated to 70° C. to be reacted for 2-5 h;

2) after the reaction, small molecules were removed by an M. W.=3500 dialysis bag, and a conductivity meter would be used for monitoring until the dialysis was completed. A water-soluble hydroxylated gadolinium metallofullerene or a water-soluble hydroxylated fullerene can be obtained from the product resulted from concentration. Upon DLS test, the average particle sizes of the water-soluble hydroxylated gadolinium metallofullerenes in aqueous solution were 140 nm, and the particle size distribution was uniform; the average particle size of the water-soluble hydroxylated fullerene in the aqueous solution was 200 nm, and the particle size distribution was uniform.

Example 3. Test of Free Radicals-Scavenging Ability of the Fullerenes

The free radicals-scavenging ability of the oil-soluble fullerenes and oil-soluble metallofullerenes was detected by electron spin resonance spectrum (ESR).

The method of producing hydroxyl radical by UV induction was adopted for testing. 50 μL of hydrogen peroxide with 39% mass concentration, 50 μL of PBS buffer solution (pH 7.4), and a small amount (0.133 mM) of lutidine N-oxide (DMPO, free radical trapping agent) were mixed. The blank control group was directly irradiated with 280 nm UV for 4 min, and the experimental group was immediately added 104, of $Gd@C_{82}$-olive oil or $C_{60}$-olive oil prepared according to Example 1 and irradiated with 280 nm of UV light for 4 min, and the radical signals were detected. ESR data was obtained, as shown in FIGS. 1 and 2.

FIG. 1 is an electron spin resonance (ESR) control diagram, where the dashed line is the blank control without $Gd@C_{82}$-olive oil, and the solid line is experimental group added the $Gd@C_{82}$-olive oil obtained in Example 1. As compared with the blank control, the ESR signal added with the $Gd@C_{82}$-olive oil was significantly attenuated, indicating that $Gd@C_{82}$-olive oil has a strong free radicals-scavenging ability.

Figure 2:
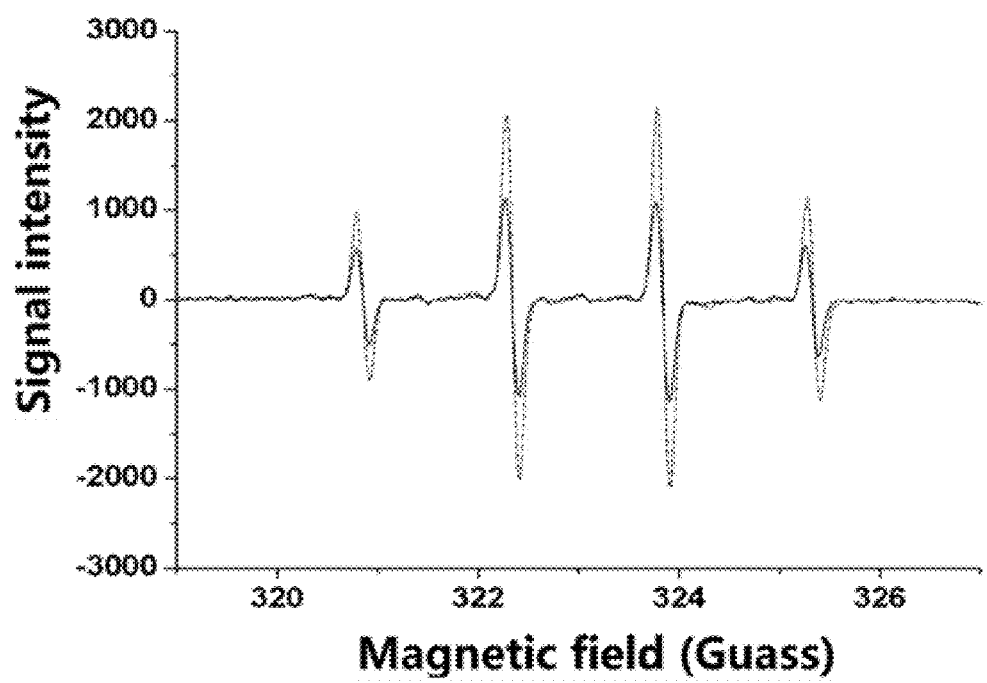
FIG. 2 is an electron spin resonance (ESR) control diagram in which the dashed line is the blank control without $C_{60}$-olive oil and the solid line is the experimental group having $C_{60}$-olive oil obtained in Example 1.

FIG. 2 is an electron spin resonance (ESR) control diagram, where the dashed line is the blank control without $C_{60}$-olive oil, and the solid line is the experimental group added $C_{60}$-olive oil obtained in Example 1. As compared with the blank control, the ESR signal added with the $C_{60}$-olive oil was significantly attenuated, indicating that $C_{60}$-olive oil has a strong free radicals-scavenging ability.

Example 4. Cell Experiment

Commonly used Hela cells were taken as a cell experimental model to verify that the $Gd@C_{82}$-olive oil and $C_{60}$-olive oil obtained in Example 1 have the ability to scavenge free radicals and protect cells.

(1) Medicament Toxicity Experiment

Hela cells were cultured in high-glucose DMEM medium containing 10% of serum, trypsinized and subcultured to a sufficient number and then were used to carried out the medicament toxicity experiment.

Figure 3:
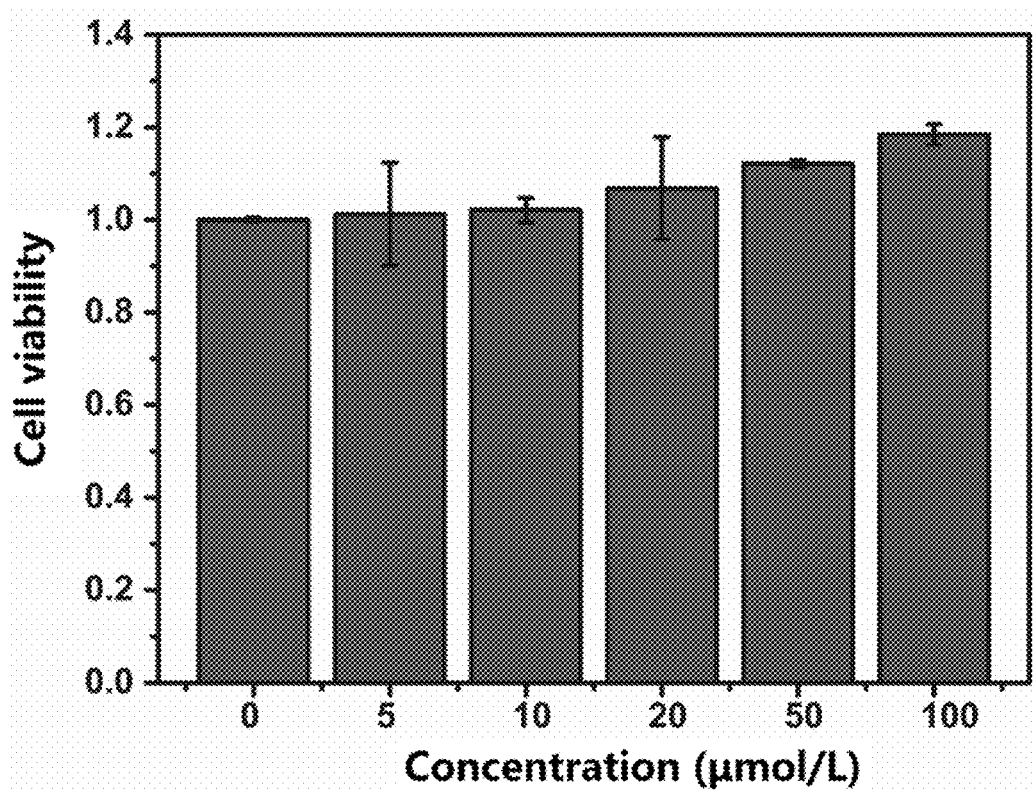
FIG. 3 shows the experimental results of medicament toxicity of the Gd@$C_{82}$-olive oil obtained in Example 1 on Hela cells.

In the cell suspension obtained by trypsinization, the cell density was $5 \times 10^4$/mL. 200 μL of cell suspension was added to each well of a 96-well plate and incubated for 24 h. The medium was aspirated, and 10% serum-containing high-glucose DMEM medium as a blank medium and $Gd@C_{82}$-olive oil medium of different concentrations were added respectively in different wells ($Gd@C_{82}$-olive oil medium of different concentrations refers to adding different amounts of the $Gd@C_{82}$-olive oil obtained in Example 1 in a blank medium to form $Gd@C_{82}$-olive oil medium of different concentrations). The concentrations of the $Gd@C_{82}$-olive oil in $Gd@C_{82}$-olive oil medium of different concentrations were 5, 10, 20, 50 and 100 μM respectively. The mixtures in different wells were incubate for 24 h, then the blank medium or $Gd@C_{82}$-olive oil medium were aspirated, the remaining cells were washed with PBS for three times and 100 μL of colorless DMED and 10 μL of CCK-8 were added to each well, the mixture in each well was incubated for 1 h and the cell activity was tested with a microplate reader. The results are as shown in FIG. 3, the cell activity of wells into which the blank medium was added as a control, that is, its cell activity is set to 1. It can be seen from FIG. 3 that after adding Gd@$C_{82}$-olive oil, the cell activity does not decrease, instead, slightly increases, which proves that Gd@$C_{82}$ has no cytotoxicity but has a certain protective effect on cells.

Figure 4:
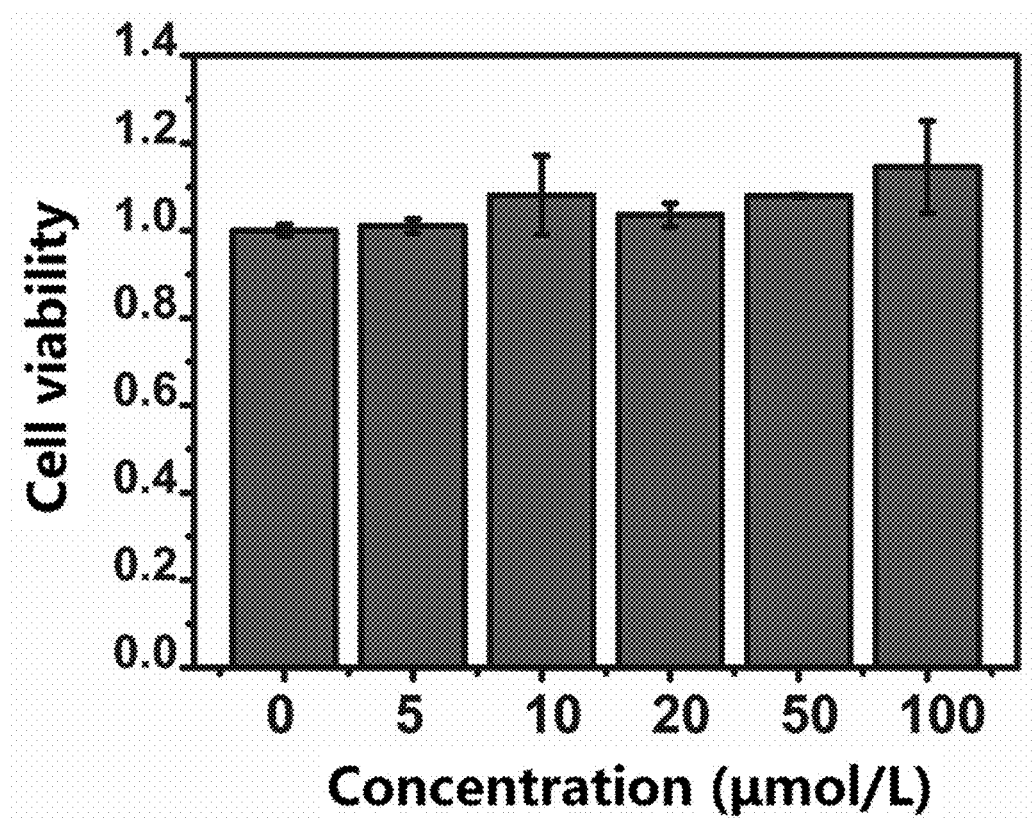
FIG. 4 shows the experimental results of medicament toxicity of the $C_{60}$-olive oil obtained in Example 1 on Hela cells.

In accordance with the same experimental procedures described above, the Gd@$C_{82}$-olive oil was replaced with $C_{60}$-olive oil for experiment. The results of the cell activity are as shown in FIG. 4, as can be seen from FIG. 4, the $C_{60}$-olive oil was non-cytotoxic, but has a certain protective effect on the cells.

(2) Free Radicals Scavenging Experiment

Figure 5:
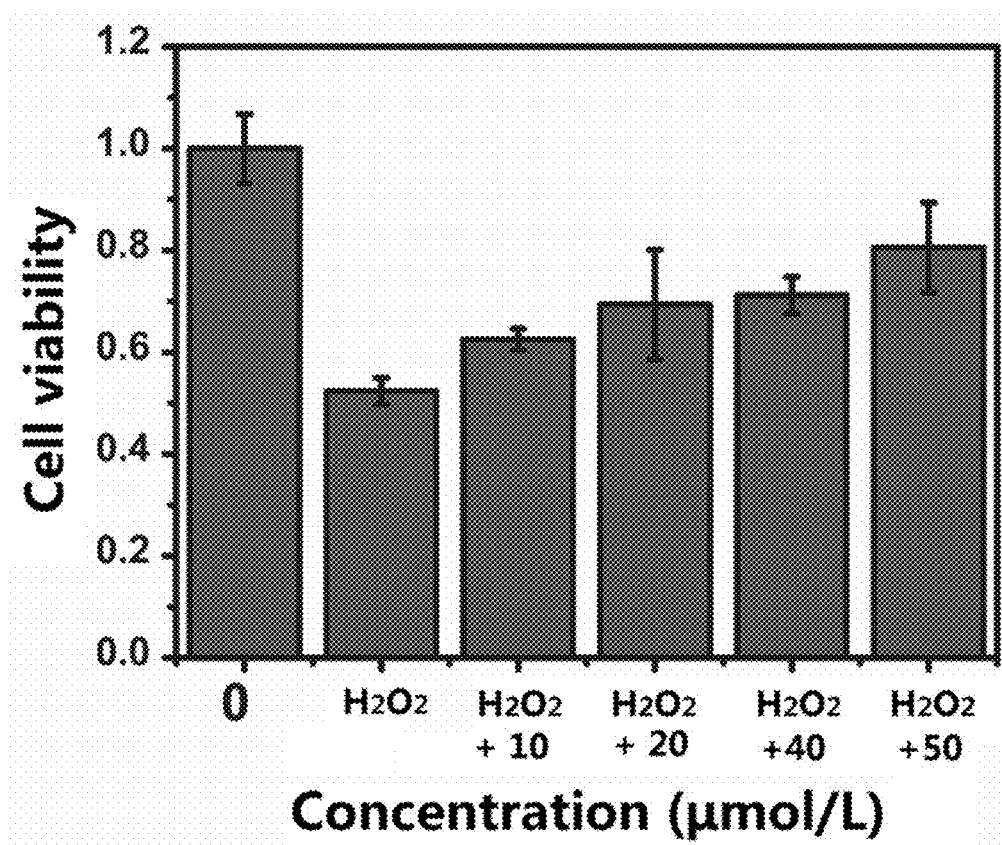
FIG. 5 is a schematic diagram showing the results of protection from hydrogen peroxide-induced cell damage by Gd@$C_{82}$-olive oil obtained in Example 1.

Hela cells were cultured in high-glucose DMEM medium containing 10% of serum, trypsinized and subcultured to a sufficient number and then carried out free radicals scavenging experiment. In the cell suspension obtained by trypsinization, the cell density was $5 \times 10^4$/mL. 200 μL of cell suspension was added to each well of a 96-well plate and incubated for 24 h, and the medium was aspirated. High-glucose DMEM medium containing 10% of serum was added in 16 random wells as a blank medium, $H_2O_2$ solution with a concentration of 150 μM was added to each of the remaining wells and incubated for 1 h, and the $H_2O_2$ solution was aspirated. Gd@$C_{82}$-olive oil medium of different concentrations were added in different wells (Gd@$C_{82}$-olive oil medium of different concentrations refers to adding different amounts of the Gd@$C_{82}$-olive oil obtained in Example 1 into a blank medium to form Gd@$C_{82}$-olive oil medium of different concentrations). The concentrations of the Gd@$C_{82}$-olive oil in Gd@$C_{82}$-olive oil medium of different concentrations were 0, 10, 20, 40 and 50 μM respectively. The mixtures in different wells were incubate for 3 h and then the blank medium or Gd@$C_{82}$-olive oil medium were aspirated, the remaining cells were washed with PBS for three times and 100 μL of colorless DMED and 10 μL of CCK-8 were added to each well, the mixture in each well was incubate for 1 h and the cell activity was tested with a microplate reader. The results are as shown in FIG. 5, the cell activity of wells into which the blank medium was added as a control, that is, its cell activity is set to 1. FIG. 5 demonstrates that the cell activity was decreased after the addition of the hydrogen peroxide, and the addition of Gd@$C_{82}$-olive oil could remove the hydroxyl radicals produced by $H_2O_2$, reduce the damage of free radicals to cells, and reduce the damage of $H_2O_2$ to cell activity.

Figure 6:
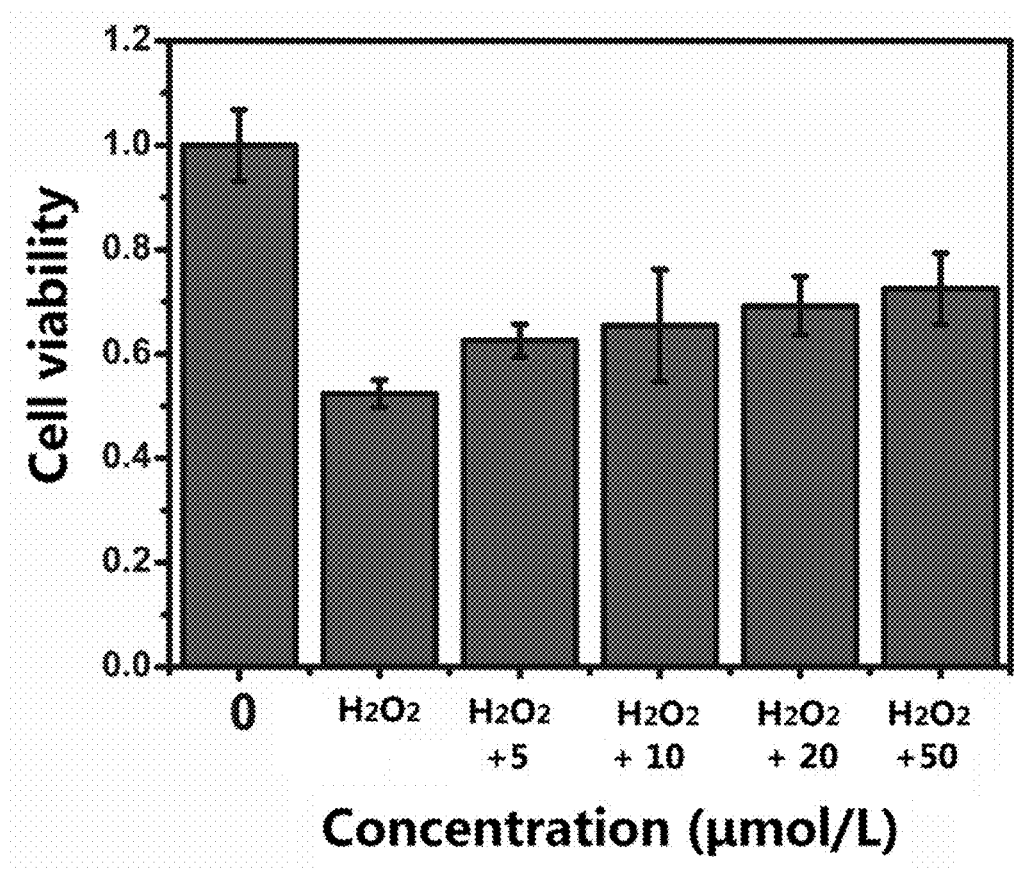
FIG. 6 is a schematic diagram showing the results of protection from hydrogen peroxide-induced cell damage by $C_{60}$-olive oil obtained in Example 1.

In accordance with the same experimental steps described above, Gd@$C_{82}$-olive oil was replaced with $C_{60}$-olive oil for the experiment. The results are as shown in FIG. 6, and the results of FIG. 6 prove that $C_{60}$-olive oil can remove hydroxyl radicals produced by $H_2O_2$, reduce the damage of free radicals to cells, and reduce the damage of $H_2O_2$ to the cell activity.

Example 5. Animal Behavioral Experiment Part 1

(1) The Establishment of Parkinson's Disease Model

Many studies have shown that there are various factors for the pathogenesis of Parkinson's disease, and neurotoxins play an important role in the pathogenetic process of Parkinson's disease. MPTP (1-Methyl-4-phenyl-1,2,3,6-tetrahydropyridine hydrochloride) was the earliest neurotoxin discovered associated with Parkinson's disease. MPTP entered the brain, and was first taken up by glial cells, then converted to MPP+ under the effect of monoamine oxidase, and MPP+ was actively taken up by dopaminergic neurons, then entered the mitochondria to inhibit the activity of respiratory chain complex I, so free radicals were produced, ATPs were depleted, leading to apoptosis. A mature MPTP-induced mouse Parkinson's disease model was used to examine the efficacy of an oil-soluble fullerene structure in the treatment of Parkinson's disease.

It has been found that C57BL/6 mice are most sensitive to MPTP, so C57BL/6 mice were used by the present disclosure for experiments.

There were 40 C57BL/6 mice in present disclosure, who were 10 weeks old, from 18 to 22 g by weight, and given intraperitoneal injection of MPTP with a concentration of 35 mg/Kg, they were injected once a day for 7 days, the mice had static tremors, reduced movements, erecting tails, piloerection and so on, proving the successful establishment of the model.

(2) Mouse Therapic Experimental Regime

Among the 40 model mice of the present disclosure, 30 were taken out for experiments. Gd@$C_{82}$-olive oil and $C_{60}$-olive oil therapic experiments were carried out for the mice suffering from Parkinson's disease. 30 experimental mice were randomly divided into group A, group B and group C with 10 in each group. Group A was Gd@$C_{82}$-olive oil experimental group, group B was $C_{60}$-olive oil experimental group, and group C was control group, and the mice were intragastrically administered. Group A was intragastrically administered with 0.1 mL of Gd@$C_{82}$-olive oil prepared in Example 1 per day, group B was intragastrically administered with 0.1 mL of $C_{60}$-olive oil prepared in Example 1 per day, and group C was intragastrically administered with the same amount of normal saline per day. The mice were administered for the whole 10 days and observed and had the behavioral experiment test.

(3) Mouse Behavioral Experiment

The present disclosure tested the therapeutic effect of the mice by the spontaneous activity counting, suspension experiments, and swimming tests.

1) Spontaneous Activity Count

The present disclosure refers to a conventional spontaneous activity counting method, a self-made perspex box of 30 cm×30 cm×15 cm was adopted, and the bottom of the box was scribed with lines into grids of 6 cm×6 cm, and the test was carried out at room temperature in a quiet and dark environment. The mice in the experimental groups and the control group were respectively tested after treatment. After the mice were adapted for 10 minutes, the number of the grids the mice had moved by and the number of times the mice had stood within 5 minutes was counted, and the average value was measured five times. The results are as shown in Table 1. As can be seen from the data in Table 1, there is a significant increase in the number of the grids the mice had moved by and the number of times the mice had stood after the mice had been treated with Gd@$C_{82}$-olive oil and $C_{60}$-olive oil, demonstrating that oil-soluble fullerenes or oil-soluble metallofullerenes can improve the behavior of the mice suffering from Parkinson's disease. As compared with the $C_{60}$-olive oil composition, Gd@$C_{82}$-olive oil composition was greater in improving the behavior of the mice suffering from Parkinson's disease.

2) Suspension Experiment

The mice in the experimental groups and the control group were respectively detected after treatment. The mice for detection were suspended on a self-made horizontal wire. If the mice grasped the wire with 2 back claws, 3 points were scored, if the wire was grasped with 1 back claw, 2 points were scored, if no wire can be grasped, 1 point was scored, the results are as shown in Table 1. As can be seen from the data in Table 1, there was a significant improvement in the hindlimb movement and coordination ability of the mice after treatment.

3) Swimming Experiment.

The mice were placed in a water tank of 20 cm×30 cm×20 cm with a temperature of from 22 to 25° C., the scoring standards are as follows: 30 points were scored for those who continuously swam within 1 min. 25 points were scored for those who swam for most of the time but just occasionally floated, 20 points were scored for those who floated for more than half the time, 15 points were scored for those who swam occasionally, and 10 points were scored for those who floated on one side. The results are as shown in Table 1. From the data in Table 1, it can be seen that the experimental groups A and B have stronger swimming ability than the control group C, which indicates that the limbs movement ability has been improved.

TABLE 1

Mouse behavioral experiment results

| Groups | The number of the grids the mice had moved by | The number of times the mice had stood | Suspension experiment | Swimming experiment |
|---|---|---|---|---|
| Experimental group A | 120.21 ± 18.21 | 35.20 ± 2.98 | 3.01 ± 0.59 | 2.98 ± 0.45 |
| Experimental group B | 110.32 ± 20.45 | 29.15 ± 3.01 | 2.85 ± 0.44 | 2.05 ± 0.60 |
| Control group C | 70.11 ± 20.34 | 19.01 ± 3.31 | 1.58 ± 0.74 | 1.49 ± 0.54 |

The present disclosure mainly adopts Gd@$C_{82}$-olive oil and $C_{60}$-olive oil as examples, and the fullerene olive oil composition and the metallofullerene olive oil composition have been proved having strong free radicals-scavenging ability through material testing, cell level testing and animal-level experiments. The tremors and incoordination of animal limbs caused by Parkinson's disease can be effectively relieved, thus Parkinson's disease can be effectively treated.

Example 6. Animal Behavioral Experiment Part 2

Levodopa is a common medicament for the treatment of Parkinson's disease. Its functional mechanism is to supplement the lack of dopamine in the brain. Clinically, it is often compatibly applied with the peripheral dopa decarboxylase inhibitor benserazide to improve efficacy. This experiment adopts a common clinical regime in which levodopa and benserazide were compatibly applied by 4:1 as positive control medicaments. A typical MPTP-induced mouse Parkinson's disease model was adopted by the experiment to examine the efficacy of the fullerene in the treatment of Parkinson's disease.

I. Experimental Materials

1. Animals: the C57/BL6J mice (male, 18-20 g) were adopted for the experiment. The mice were raised in an environment of room temperature 24±2° C., a light-dark 12-hour cycle alternation was maintained and adequate food and clean drinking water were supplied. The mice were adopted for experiments after being raised for more than 5 days.

2. Compounds 2.1. Modeling Medicaments

Name: MPTP (1-Methyl-4-phenyl-1,2,3,6-tetrahydropyridine hydrochloride);

Property: off-white powder;

Product number: $M_{0896}$;

Specification: 100 mg/bottle;

Storage conditions: room temperature, sealing, drying, and protection from light;

Provider: sigma.

2.2. Positive Control Medicaments

Name: Levodopa (levodopa, L-DA);

Property: white powder;

Lot number: MKBQ9185V;

Specification: 5 g/bottle;

Storage conditions: room temperature, sealing, drying, and protection from light;

Provider: sigma.

Name: Benserazide;

Property: off-white powder;

Lot number: BCBN0530V;

Specification: 1 g/bottle;

Storage conditions: from 2 to 8° C., sealing, drying, and protection from light;

Provider: sigma.

2.3. Test Compounds

Name: $C_{60}$-olive oil obtained in Example 1 (hereinafter abbreviated as fullerene);

Property: brown-red liquid;

Sample content: 870 mg/L.

3. The Above Compound Preparation Method

Compound Preparation Method

| Name | Preparation | Subpackage | Storage | Pre-administration |
|---|---|---|---|---|
| Modeling medicaments MPTP | 4 ml of sodium chloride injection was injected into an 100-mg bottle, and shaken to fully dissolve the powder, with the mother liquor | — | 4° C., sealed and protected from light. | Before each administration, 25 mg/ml of MPTP mother liquor was diluted with sodium chloride injection to a 2.5 mg/ml of liquid for use and mixed |

| Name | Preparation | Subpackage | Storage | Pre-administration |
|---|---|---|---|---|
| | concentration being 25 mg/ml. (25 mg/kg MPTP) | | | well and injected subcutaneously. The administration volume was 10 ml/kg. |
| Positive medicament levodopa (L-DA) | A certain amount of L-DA powder was weighed and sodium chloride injection was added to a final concentration of 1 mg/ml. (10 mg/kg L-DA) | — | Freshly prepared every day. | Before each administration, the medicaments were mixed well and injected intraperitoneally. The administration volume was 10 ml/kg. |
| Positive medicament benserazide (Be) | A certain amount of benserazide powder was weighed and sodium chloride injection was added to a final concentration of 0.25 mg/ml. (2.5 mg/kg Benserazide) | — | Freshly prepared every day. | Before each administration, the medicaments were mixed well and injected intraperitoneally. The administration volume was 10 ml/kg. |
| Test medicament ($C_{60}$ - olive oil) | The mother liquor of fullerene with a concentration of 870 mg/L was diluted with olive oil to 0.2262 mg/ml, 0.1131 mg/ml, and 0.05655 mg/ml of liquid for use. | — | sealed and protected from light. | Before each administration, the medicaments were mixed well and intragastrically administered. The administration volume of diluted liquid for use of the fullerene was 10 ml/kg. |

II. Experimental Method

1. Experimental Grouping

A total of 72 C57 mice were randomly divided into 7 groups:

| Serial number | Group | Meidcament name | Group for short | Animal number |
|---|---|---|---|---|
| 1 | Normal saline control group | Normal saline | Control group | 10 |
| 2 | Modeling group | 25 mg/kg MPTP | Modeling group | 11 |
| 3 | Olive oil group | Olive oil | Olive oil group | 10 |
| 4 | Positive medicaments group | 10 mg/kg L-dopa + 2.5 mg/kg Benserazide | L-dopa + Benserazide group | 11 |
| 5 | Test compound group | 0.5655 mg/kg fullerene | 0.5655 mg/kg of test compound fullerene group | 10 |
| 6 | | 1.131 mg/kg fullerene | 1.131 mg/kg of test compound fullerene group | 10 |
| 7 | | 2.262 mg/kg fullerene | 2.262 mg/kg of test compound fullerene group | 10 |

Figure 7:
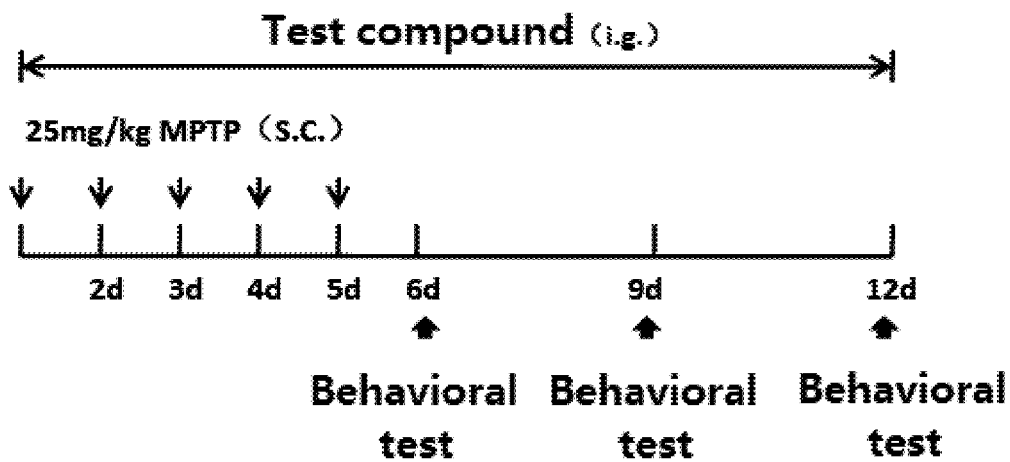
FIG. 7 is an experimental flow chart of the modeling and administration in Example 6.

2. Experimental Regime 2.1. Normal saline was adopted for the control group for modeling and administration, except for replacing the corresponding medicament with the normal saline, the control group's modeling and administration methods are the same as those of the other 6 groups. The other 6 groups were injected subcutaneously once a day with 25 mg/kg of MPTP for 5 days. During the modeling period, the positive medicaments or test medicament or olive oil or normal saline was also given. After modeling, the MPTP was stopped being given, the test medicament or positive medicaments or olive oil or normal saline was still given for 7 days. Administration volume was 10 ml/kg each time. The experimental flow chart for modeling and administration was as shown in FIG. 7, and the administration was particularly as shown in the following table.

| Group | Treating medicament name and its drug-delivery way | Modeling medicament name and its drug-delivery way |
| --- | --- | --- |
| Control group | Normal saline (i.p.) | Normal saline (s.c.) |
| Modeling group | Normal saline (i.p.) | 25 mg/kg MPTP (s.c.) |
| Olive oil group | Olive oil (i.p.) | |
| Positive medicaments group | 10 mg/kg L-dopa(i.p.) + 2.5 mg/kg Benserazi (i.p.) | |
| Test compound group | 0.5655 mg/kg fullerene (i.g.) 1.131 mg/kg fullerene (i.g.) 2.262 mg/kg fullerene (i.g.) | |

2.2. On the 5th, 9th and 12th days of the experiment, the behavioral test of the spontaneous activity of the mice was performed; On the 6th, 9th, and 12th days of the experiment, mice were tested for climbing poles and rotarod behaviors.

3. Behavioral Testing Method 3.1. Mouse Spontaneous Activity was Tested by an Open-Field Method An open box experimental apparatus used for the open-field method was TS EMulti Conditioning systems. The length, width and height of the inner box were 45 cm×45 cm×33 cm respectively, and the camera recorded animal activities. In this experiment, the mice were performed spontaneous activity behavioral tests on the 5th, 9th and 12th days of the experiment. The experiment was conducted in a quiet room. The mice were placed in the center of the open box. The test lasted for 5 minutes, and the mice were observed for their activity time, activity distance, vertical activity time (mice standing time) within 5 minutes. The open box was thoroughly cleaned and the next mouse was observed.

3.2. Bradykinesia of Mice was Tested by the Pole Test

The pole test was used to test typical behavioral symptoms in Parkinson's disease-bradykinesia. In this experiment, the mice were performed behavioral tests on the 6th, 9th, and 12th days respectively. The mouse with the head upwards was placed gently on the top of a rough pole (8 mm in diameter and 55 cm in height). The time taken by the mice from moving from the top of the rod until the head was downwards was recorded as the latent period T-turn, and the time taken by the mice from moving downward until the limbs all reached the bottom of the rod was recorded as the down-climbing time T-LA, the time over 30 s was recorded as 30 s. Each mouse was tested 5 times and an average value was obtained.

3.3. Rotarod Test was Used to Test the Motor Coordination Ability of Mice

The rotarod was divided into 5 horizontal sections, each was separated by a partition to ensure that the animals were not affected by each other. Rotarod speed was set to 28 rpm/2 min. The mouse was placed on a 1.25 inch diameter roller and the switch was turned on. When timing started, the time taken by the mouse from starting rotating the rotarod until the mouse fell off from the roller was recorded as the latent period (i.e., the first time of falling off) as a measurement of the motor coordination ability of mice. Each mouse was tested 3 times and an average value was obtained. The mice were performed rotarod tests on the 6th, 9th, and 12th days of the experiment.

III. Experimental Results

Figure 8:
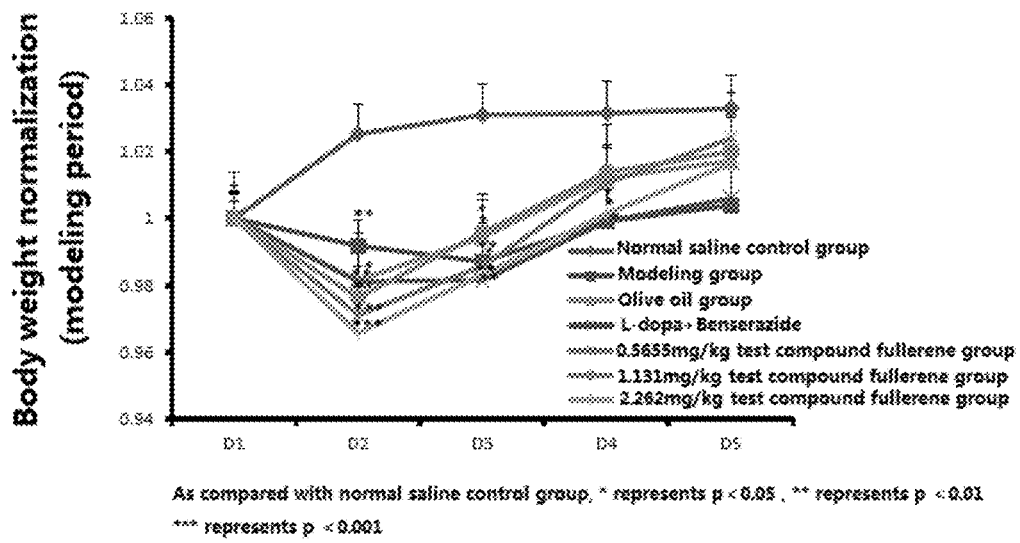
FIG. 8 is a graph showing changes in body weight of experimental animals during MPTP modeling in Example 6.
Figure 9:
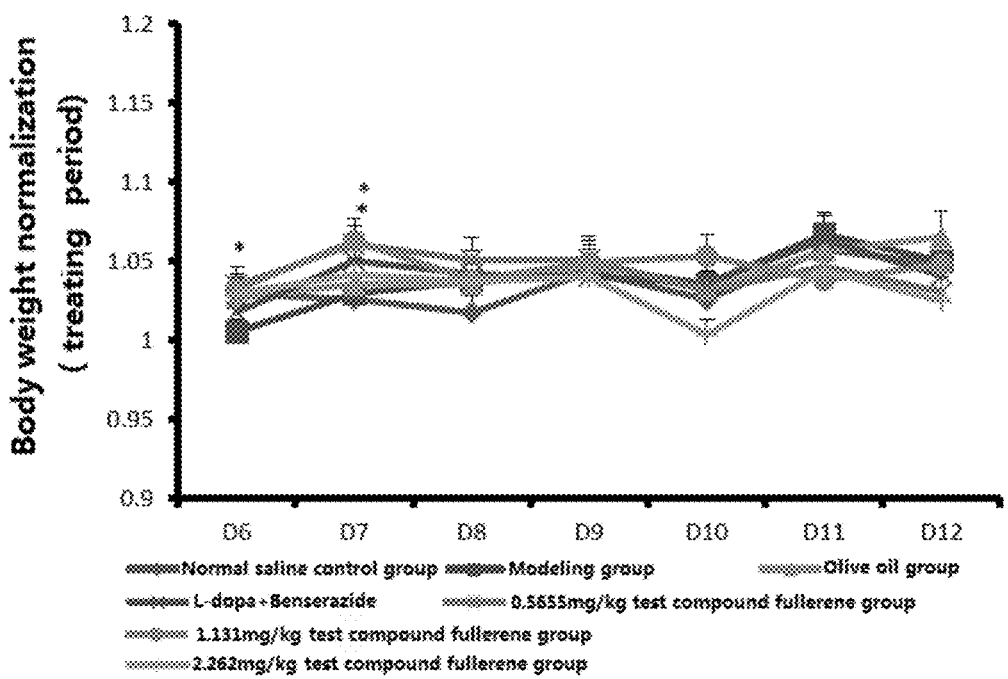
FIG. 9 is a graph showing changes in body weight of experimental animals during MPTP treatment in Example 6.
Figure 10:
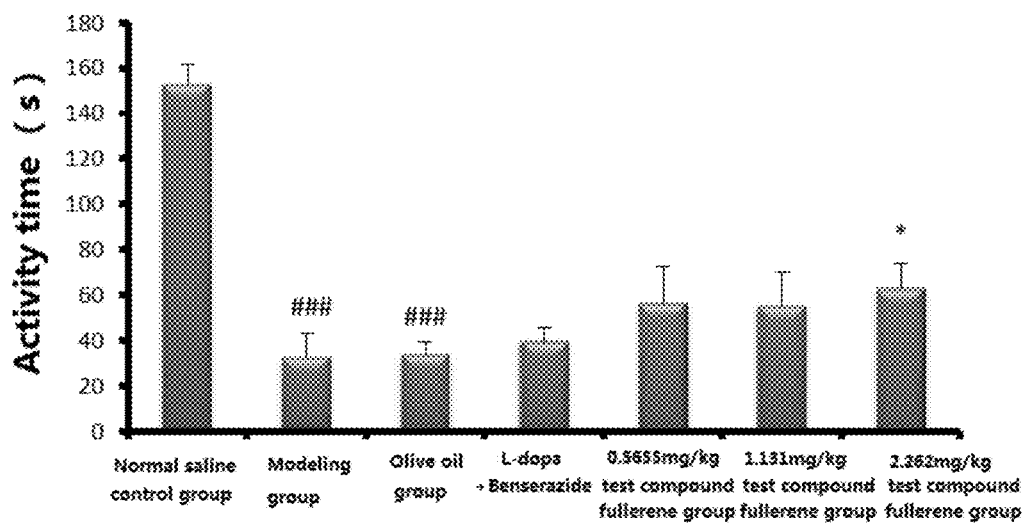
FIG. 10 is a graph showing the effect of the $C_{60}$-olive oil obtained in Example 1 on the activity time of the model mice suffering from MPTP-induced Parkinson's disease in Example 6 (day 5).
Figure 11:
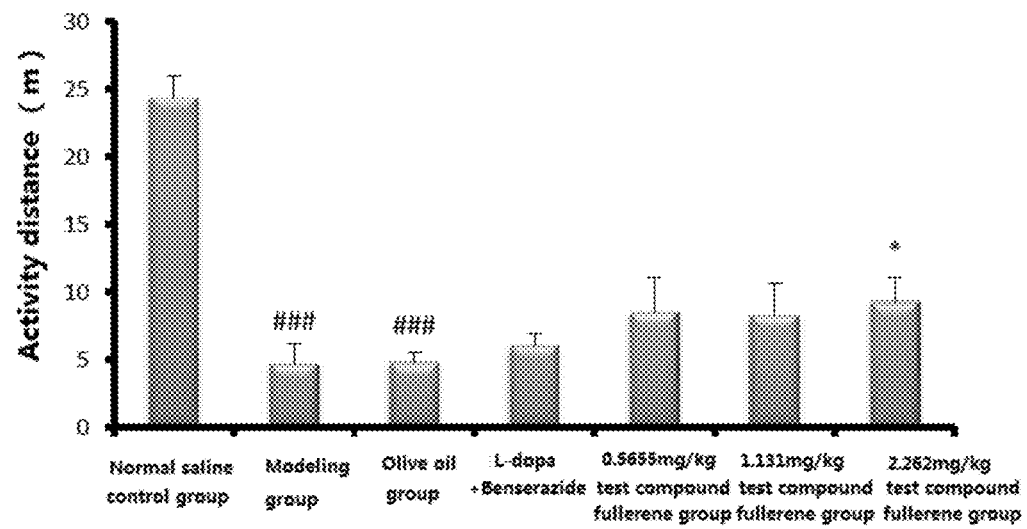
FIG. 11 is a graph showing the effect of the $C_{60}$-olive oil obtained in Example 1 on the activity distance of the model mice suffering from MPTP-induced Parkinson's disease in Example 6 (day 5).
Figure 12:
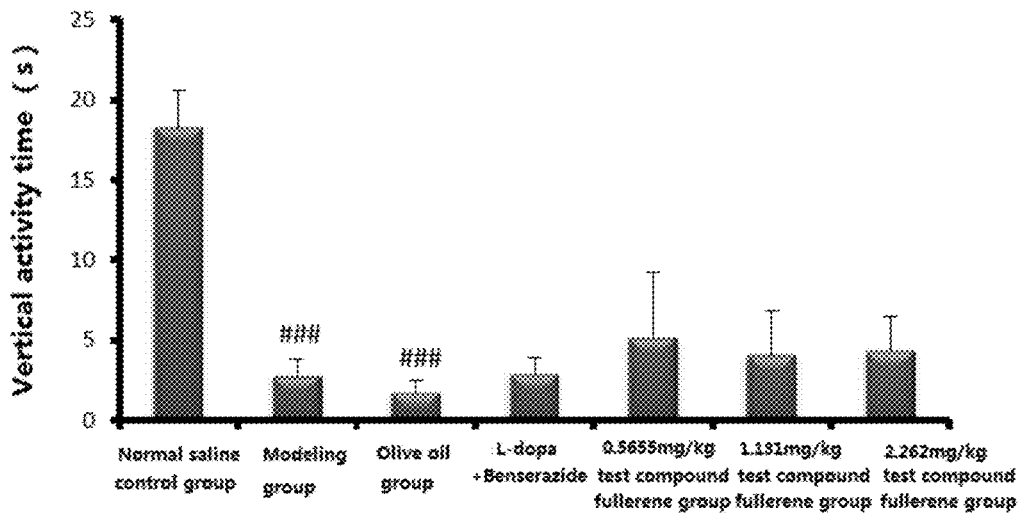
FIG. 12 is a graph showing the effect of the $C_{60}$-olive oil obtained in Example 1 on the vertical activity time of the model mice suffering from MPTP-induced Parkinson's disease in Example 6 (day 5).
Figure 13:
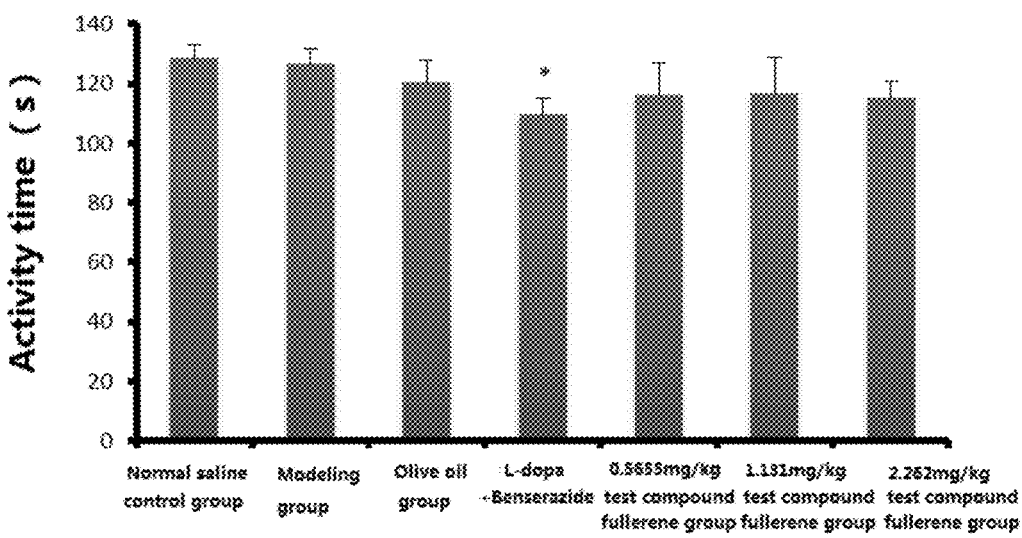
FIG. 13 is a graph showing the effect of the $C_{60}$-olive oil obtained in Example 1 on the activity time of the model mice suffering from MPTP-induced Parkinson's disease in Example 6 (day 9).
Figure 14:
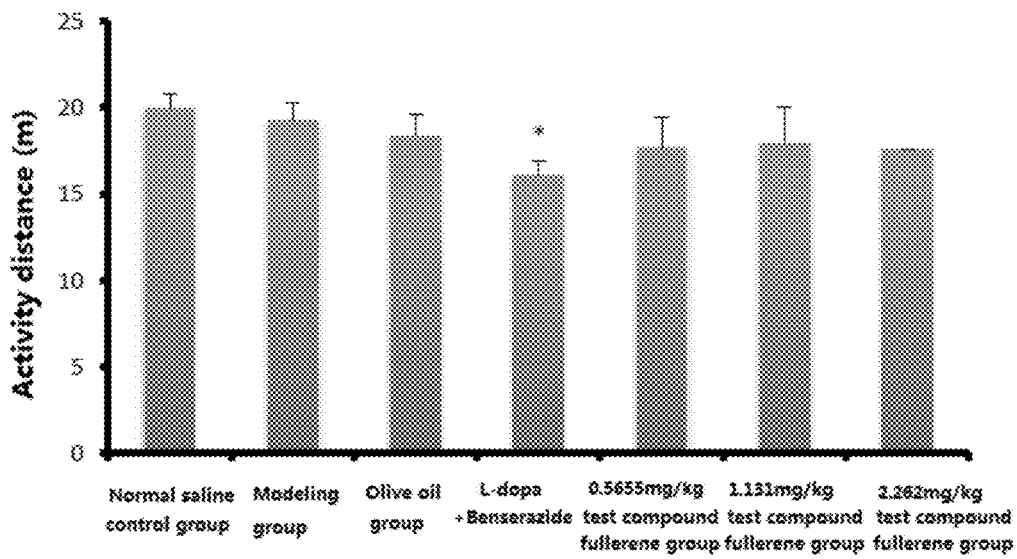
FIG. 14 is a graph showing the effect of the $C_{60}$-olive oil obtained in Example 1 on the activity distance of the model mice suffering from MPTP-induced Parkinson's disease in Example 6 (day 9).
Figure 15:
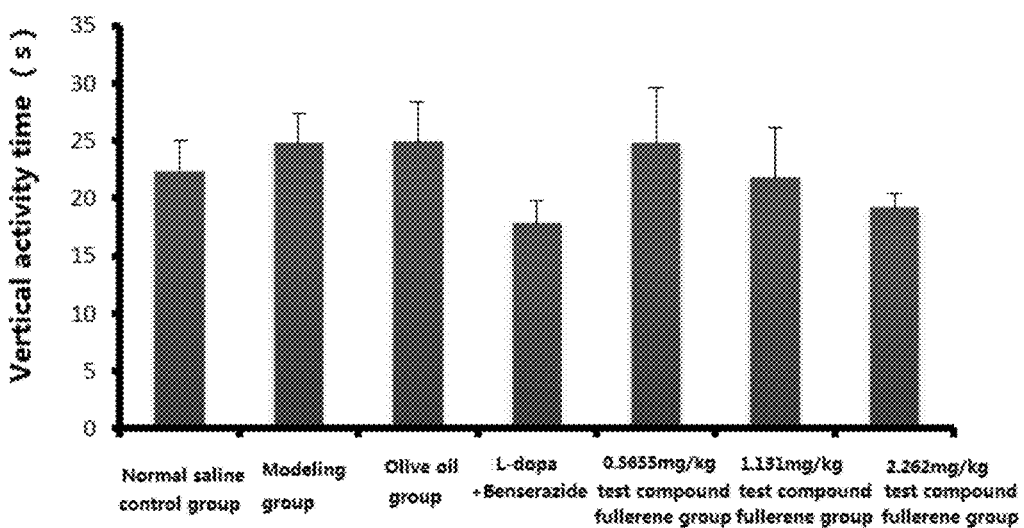
FIG. 15 is a graph showing the effect of the $C_{60}$-olive oil obtained in Example 1 on the vertical activity time of the model mice suffering from MPTP-induced Parkinson's disease in Example 6 (day 9).
Figure 16:
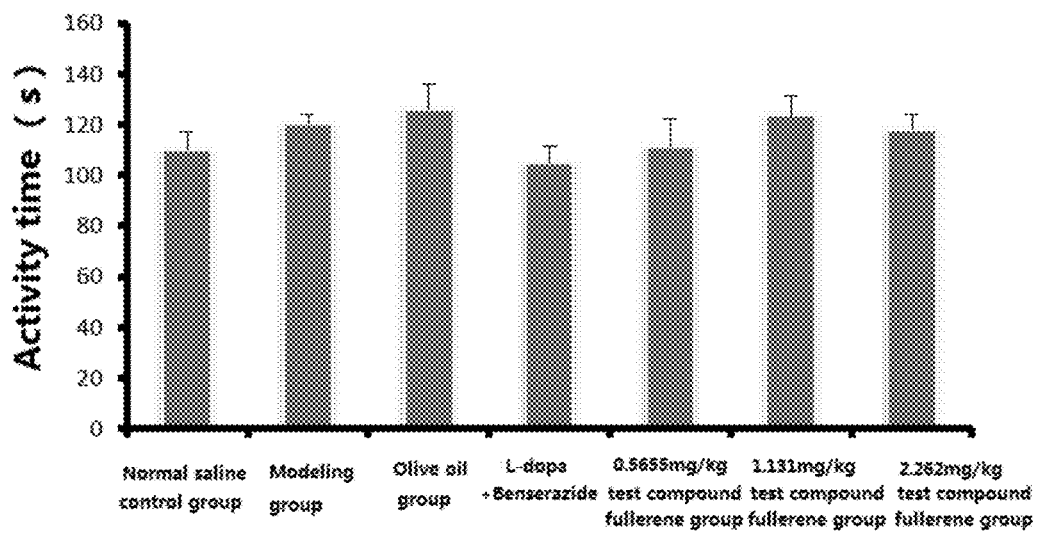
FIG. 16 is a graph showing the effect of the $C_{60}$-olive oil obtained in Example 1 on the activity time of the model mice suffering from MPTP-induced Parkinson's disease in Example 6 (day 12).
Figure 17:
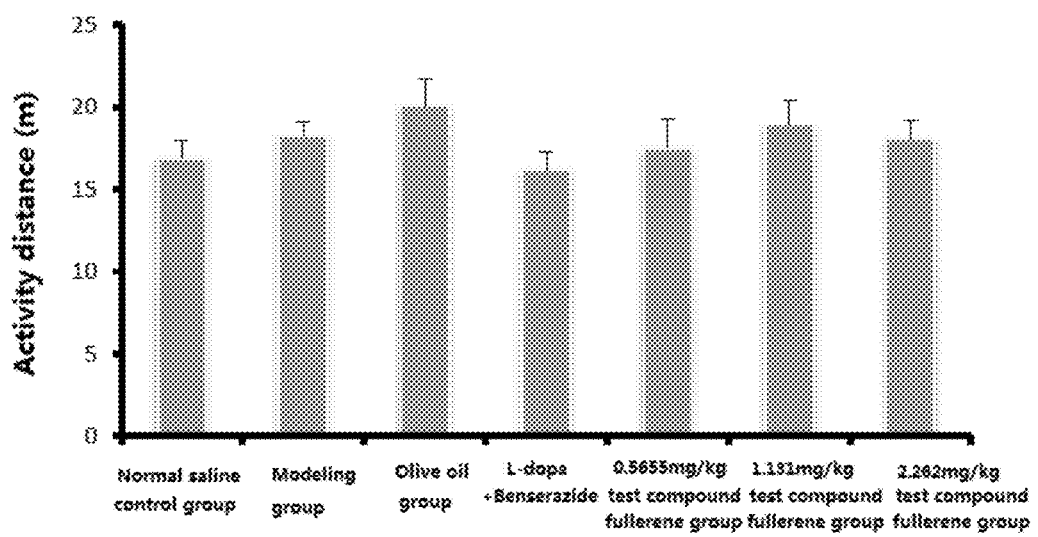
FIG. 17 is a graph showing the effect of the $C_{60}$-olive oil obtained in Example 1 on the activity distance of the model mice suffering from MPTP-induced Parkinson's disease in Example 6 (day 12).
Figure 18:
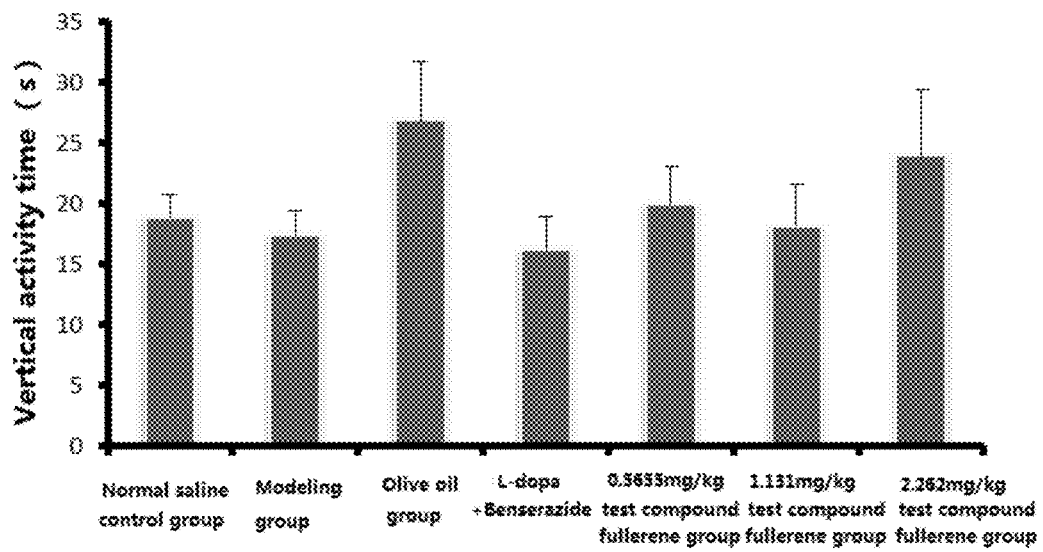
FIG. 18 is a graph showing the effect of the $C_{60}$-olive oil obtained in Example 1 on the vertical activity time of the model mice suffering from MPTP-induced Parkinson's disease in Example 6 (day 12).
Figure 19:
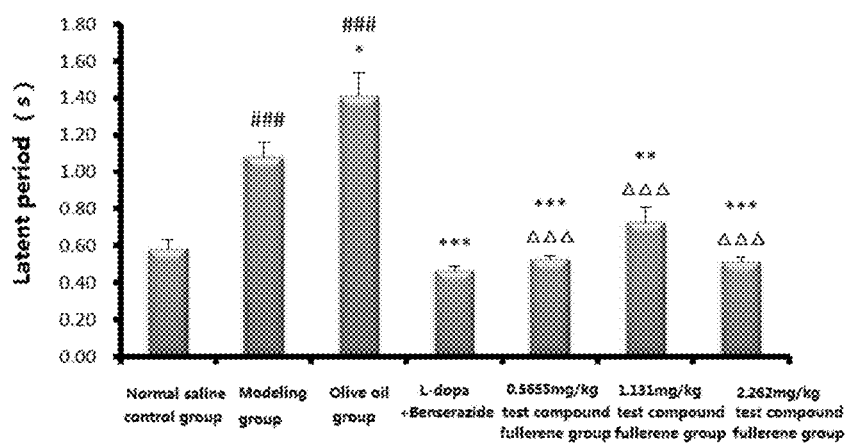
FIG. 19 is a graph showing the latent period of mice tested by the pole test after the mice administration of day 6 in Example 6.
Figure 22:
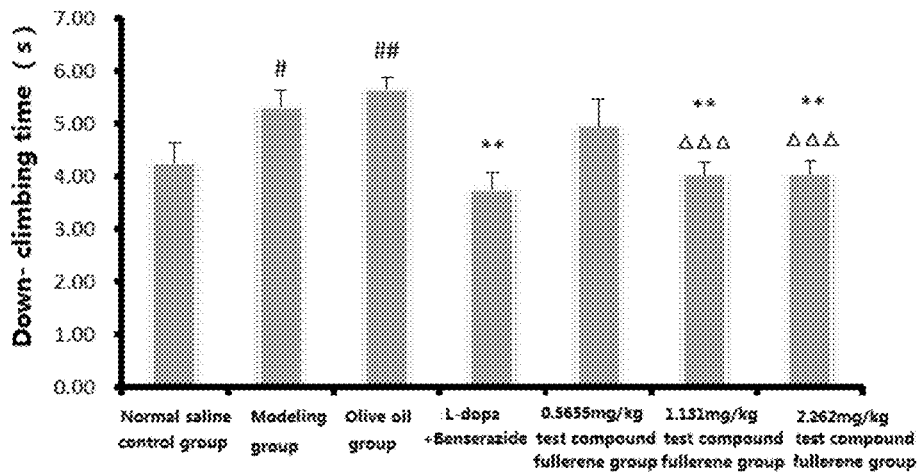
FIG. 22 is a graph showing the down-climbing time of mice tested by the pole test after the mice administration of day 9 in Example 6.
Figure 23:
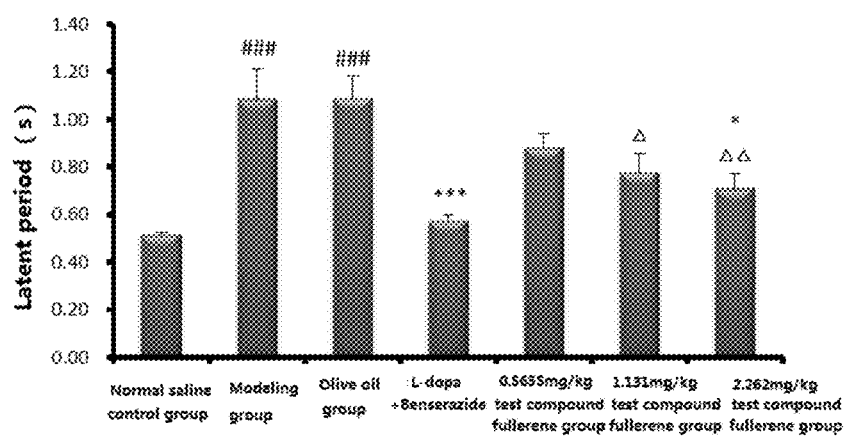
FIG. 23 is a graph showing the latent period of mice tested by the pole test after the mice administration of day 12 in Example 6.
Figure 24:
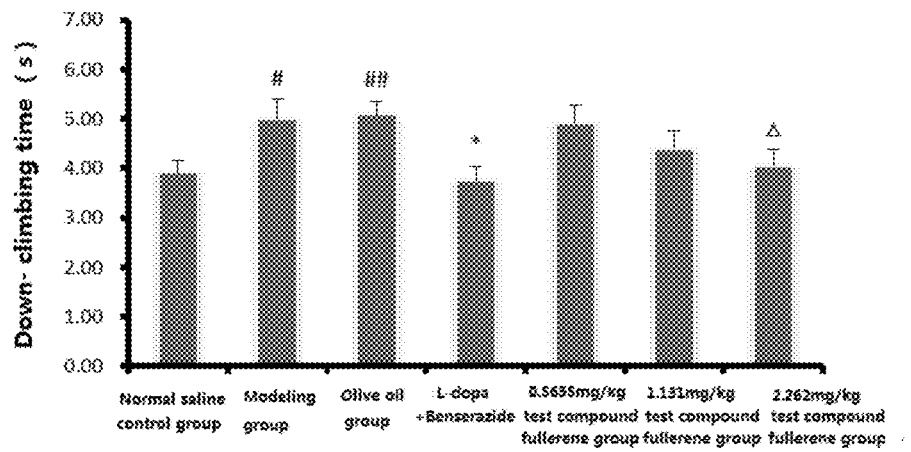
FIG. 24 is a graph showing the down-climbing time of mice tested by the pole test after the mice administration of day 12 in Example 6.

1 Changes in Body Weight of the Experimental Animals after MPTP Modeling and Medication Treatment On the second day of MPTP modeling, the body weights of the 6 groups of mice except for the normal saline control group of mice were significantly reduced, as compared with the normal saline control group of mice, the difference was significant ($p<0.05$-$0.001$); On the fourth day, weight gain was gradually recovered (see FIG. 8). After the modeling, i.e., on the 6th day of the experiment, weight gain of the mice in each group and in the normal saline control group tends to be consistent, and weight gain of mice in the test compound groups and in the olive oil group also tends to be consistent, and there was no statistically significant difference. The weight gain of 0.5655 mg/kg of test compound fullerene group (6th and 7th days of the experiment) and 1.131 mg/kg of test compound fullerene group (6th day of the experiment) was higher than that of the modeling group, and there was a significant difference as compared with the modeling group ($p<0.05$); There was no significant difference in the weight gain of the mice in other groups as compared with that of the modeling group. (See FIG. 9)

2. Behavioral Experiment 2.1. Mouse Spontaneous Activity was Tested by the Open-Field Method On the 5th, 9th, and 12th days of the experiment, i.e., the 5th day of the modeling (i.e., 5th day of administration), the 4th day after the modeling (i.e., the 9th day of administration) and the 7th day after the modeling (i.e., the 12th day of administration), the mice's spontaneous activity was evaluated. The results were as shown in Table 2, Table 3, and Table 4 and in FIG. 10-FIG. 18. On the 5th day of the experiment, the ambulatory activities of the mice in the modeling group and the olive oil group were lower than that of the normal saline control group, showing a decrease in the horizontal activity time, and activity distance, as well as the vertical activity time, as compared with the normal saline control group, there was an extremely significant difference ($p<0.001$). The ability of the mice in performing ambulatory activities in the positive medicament group and the test compound fullerene groups of different doses was higher than that in the modeling group, but there was no significant difference as compared with the modeling group. The ability of the mice in performing ambulatory activities in the olive oil group was similar to that of the modeling group, and there was no statistically significant difference. The ability of the mice in performing ambulatory activities in the test compound fullerene groups was higher than that of the olive oil group, as compared with the mice in the olive oil group, there was a significant difference in the activity time and activity distance of the mice in the group of 2.262 mg/kg of test compound fullerene group ($p<0.05$). On the 9th day of the experiment, the ambulatory ability of the mice in each group had gradually recovered. There was no significant difference among the mice in the modeling group, the olive oil group and the normal saline control group. There was a significant difference in the activity time and activity distance between the mice in the positive medicament group and the modeling group ($p<0.05$). There was no significant difference in the ability of the mice in the modeling group and the test compound fullerene group in performing spontaneous activity as compared with the mice in the olive oil group. On the 12th day of the experiment, the horizontal activity time, activity distance and vertical activity time of mice in the modeling group and the olive oil group were all close to those of the mice in the normal saline control group. There was no statistically significant difference, and the results suggest that the ability of the mice in the modeling group in performing spontaneous activity may have been recovered.

FIGS. 19-24. The latent period T-turn and down-climbing time T-LA of the mice in the modeling group and the olive oil group were significantly prolonged, showing a significant difference as compared with that in the normal saline control group ($p<0.05$-$0.001$). On the 6th day of the experiment, the T-turn time and the T-LA time of the mice in the positive medicament L-dopa+Benserazide group were significantly shortened, as compared with the modeling group, there was an extremely significant difference ($p<0.001$); the latent period of the mice in the olive oil group was longer than that

TABLE 2

Effect of fullerene on the spontaneous activity of the model mice suffering from MPTP-induced PD (D 5)

| Group | Activity time (s) | Activity distance (s) | Vertical activity time (s) |
|---|---|---|---|
| Normal saline control group | 152.70 ± 9.00 (n = 10) | 24.39 ± 1.60 (n = 10) | 18.27 ± 2.33 (n = 10) |
| Modeling group | 32.22 ± 10.54### (n = 10) | 4.66 ± 1.47###(n = 10) | 2.74 ± 1.04### (n = 10) |
| Olive oil group | 33.67 ± 5.40### (n = 10) | 4.81 ± 0.72###(n = 10) | 1.64 ± 0.84### (n = 10) |
| L-dopa + Benserazide | 39.56 ± 5.99 (n = 11) | 6.06 ± 0.87 (n = 11) | 2.85 ± 1.09 (n = 11) |
| 0.5655 mg/kg test compound fullerene group | 56.33 ± 15.97 (n = 10) | 8.49 ± 2.55 (n = 10) | 5.12 ± 4.07 (n = 10) |
| 1.131 mg/kg test compound fullerene group | 55.12 ± 14.92 (n = 10) | 8.29 ± 2.37 (n = 10) | 4.03 ± 2.84 (n = 10) |
| 2.262 mg/kg test compound fullerene group | 62.86 ± 11.07* (n = 10) | 9.30 ± 1.76* (n = 10) | 4.30 ± 2.20 (n = 10) |

As compared with normal saline control group,
represents $p < 0.001$;
as compared with olive oil group,
*represents $p < 0.05$

TABLE 3

Effect of fullerene on the spontaneous activity of the model mice suffering from MPTP-induced PD (D 9)

| Group | Activity time (s) | Activity distance (s) | Vertical activity time (s) |
|---|---|---|---|
| Normal saline control group | 128.22 ± 4.89 (n = 10) | 19.95 ± 0.83 (n = 10) | 22.32 ± 2.71 (n = 10) |
| Modeling group | 126.25 ± 5.41 (n = 11) | 19.32 ± 0.95 (n = 11) | 24.73 ± 2.64 (n = 11) |
| Olive oil group | 120.39 ± 7.53 (n = 10) | 18.39 ± 1.24 (n = 10) | 24.87 ± 3.50 (n = 10) |
| L-dopa + Benserazide | 109.57 ± 5.39* (n = 11) | 16.05 ± 0.83* (n = 11) | 17.82 ± 2.02 (n = 11) |
| 0.5655 mg/kg test compound fullerene group | 115.87 ± 10.80 (n = 10) | 17.70 ± 1.78 (n = 10) | 24.76 ± 4.90 (n = 10) |
| 1.131 mg/kg test compound fullerene group | 116.57 ± 12.20 (n = 10) | 17.90 ± 2.14 (n = 10) | 21.78 ± 4.36 (n = 10) |
| 2.262 mg/kg test compound fullerene group | 115.27 ± 5.37 (n = 10) | 17.56 ± 1.12 (n = 10) | 19.19 ± 1.23 (n = 10) |

As compared with modeling group,
*represents $p < 0.05$

TABLE 4

Effect of fullerene on the spontaneous activity of the model mice suffering from MPTP-induced PD (D 12)

| Group | Activity time (s) | Activity distance (s) | Vertical activity time (s) |
|---|---|---|---|
| Normal saline control group | 110.09 ± 7.11 (n = 10) | 16.92 ± 1.09 (n = 10) | 18.94 ± 1.87 (n = 10) |
| Modeling group | 120.13 ± 4.03 (n = 11) | 18.31 ± 0.77 (n = 11) | 17.47 ± 1.98 (n = 11) |
| Olive oil group | 126.07 ± 9.85 (n = 10) | 20.09 ± 1.61 (n = 10) | 26.89 ± 4.84 (n = 10) |
| L-dopa + Benserazide | 105.11 ± 6.36 (n = 11) | 16.15 ± 1.15 (n = 11) | 16.22 ± 2.74 (n = 11) |
| 0.5655 mg/kg test compound fullerene group | 111.17 ± 10.95 (n = 10) | 17.49 ± 1.79 (n = 10) | 20.01 ± 3.00 (n = 10) |
| 1.131 mg/kg test compound fullerene group | 123.53 ± 7.78 (n = 10) | 18.93 ± 1.45 (n = 10) | 18.16 ± 3.49 (n = 10) |
| 2.262 mg/kg test compound fullerene group | 118.00 ± 5.90 (n = 10) | 18.08 ± 1.10 (n = 10) | 23.99 ± 5.46 (n = 10) |

2.2. Pole Test

On the 6th, 9th, and 12th days of the experiment, the mice were tested for pole behaviors and tested for activity coordination. The results were as shown in Table 5, Table 6 and of the modeling group, and there was a significant difference ($p<0.05$); as compared with the mice in the modeling group, there was a significant difference in the latent period and down-climbing time of the mice in each dose of test compound fullerene group (p<0.05-0.001). As compared with the mice in the olive oil group, there was a significant difference in the latent period and down-climbing time of the mice in each dose of test compound fullerene group (p<0.05-0.001). On the 9th day of the experiment, the T-turn time and the T-LA time of the mice in the positive medicament group and the different dose of test compound fullerene groups were significantly shortened, as compared with the modeling group, there was a significant difference (p<0.01-0.001); the latent period of the mice in the olive oil group was longer than that of the modeling group, and there was a significant difference (p<0.05); as compared with the mice in the modeling group, there was a significant difference in the latent period of the mice in each dose of fullerene groups and down-climbing time of the mice in 1.131 mg/kg and 2.262 mg/kg of test compound fullerenes groups (p<0.01-0.001). As compared with the mice in the olive oil group, there was an extremely significant difference in the T-turn time of the mice in each dose of fullerene groups and the T-LA time of the mice in 1.131 mg/kg and 2.262 mg/kg of test compound fullerene groups (p<0.001). On the 12th day of the experiment, the T-turn and T-LA times of the mice in the positive medicament group and each dose of the test compound fullerene groups were shortened, as compared with the modeling group, there was a significant difference in the T-turn and T-LA times of the mice in the positive medicament group and the T-turn time of the mice in 2.262 mg/kg of test compound fullerene group (p<0.05-0.001). As compared with the olive oil group, there was a significant difference in the T-turn time of the mice in 1.131 mg/kg and 2.262 mg/kg of test compound fullerene groups and the T-LA time of the mice in 2.262 mg/kg of test compound fullerene group (p<0.01-0.05). The results showed that fullerenes can significantly relieve MPTP-induced bradykinesia and stiffness in mice and improve animal motor coordination ability.

TABLE 5

Effect of fullerene on latent period of pole behavior of the model mice suffering from MPTP-induced PD (S)

| Group | 6th day | 9th day | 12th day | Animal number (n) |
| --- | --- | --- | --- | --- |
| Normal saline control group | 0.58 ± 0.05 | 0.53 ± 0.04 | 0.51 ± 0.01 | 10 |
| Modeling group | 1.08 ± 0.08### | 0.92 ± 0.09### | 1.08 ± 0.13### | 11 |
| Olive oil group | 1.41 ± 0.13###* | 1.28 ± 0.12###* | 1.09 ± 0.09### | 10 |
| L-dopa + Benserazide | 0.46 ± 0.02*** | 0.55 ± 0.03*** | 0.57 ± 0.03*** | 11 |
| 0.5655 mg/kg test compound fullerene group | 0.52 ± 0.02*ΔΔΔ | 0.55 ± 0.04ΔΔΔ | 0.88 ± 0.06 | 10 |
| 1.131 mg/kg test compound fullerene group | 0.72 ± 0.08ΔΔΔ | 0.55 ± 0.04ΔΔΔ | 0.78 ± 0.08Δ | 10 |
| 2.262 mg/kg test compound fullerene group | 0.51 ± 0.03*ΔΔΔ | 0.47 ± 0.0*ΔΔΔ | 0.71 ± 0.06*ΔΔ | 10 |

As compared with normal saline control group,
represents $p < 0.001$;
as compared with modeling group,
*represents $p < 0.05$,
**represents $p < 0.01$,
***represents $p < 0.001$;
as compared with olive oil group,
Δrepresents $p < 0.05$,
ΔΔrepresents $p < 0.01$,
ΔΔΔrepresents $p < 0.001$

TABLE 6

Effect of fullerene on down-climbing time of pole behavior of the model mice suffering from MPTP-induced PD (S)

| Group | 6th day | 9th day | 12th day | Animal number (n) |
| --- | --- | --- | --- | --- |
| Normal saline control group | 3.98 ± 0.18 | 4.26 ± 0.37 | 3.92 ± 0.24 | 10 |
| Modeling group | 5.18 ± 0.26## | 5.32 ± 0.33# | 4.99 ± 0.41# | 11 |
| Olive oil group | 5.27 ± 0.17### | 5.66 ± 0.23## | 5.08 ± 0.28## | 10 |
| L-dopa + Benserazide | 3.78 ± 0.25*** | 3.76 ± 0.33** | 3.74 ± 0.29* | 11 |
| 0.5655 mg/kg test compound fullerene group | 4.43 ± 0.20*ΔΔ | 4.96 ± 0.50 | 4.92 ± 0.36 | 10 |
| 1.131 mg/kg test compound fullerene group | 4.16 ± 0.24ΔΔ | 4.04 ± 0.25 ΔΔΔ | 4.40 ± 0.36 | 10 |
| 2.262 mg/kg test compound fullerene group | 3.61 ± 0.25*** ΔΔΔ | 4.05 ± 0.26** ΔΔΔ | 4.05 ± 0.34Δ | 10 |

As compared with normal saline control group,
represents $p < 0.01$,
represents $p < 0.001$;
as compared with modeling group,
*represents $p < 0.05$,
**represents $p < 0.01$,
***represents $p < 0.001$;
as compared with olive oil group,
Δrepresents $p < 0.05$,
ΔΔrepresents $p < 0.01$,
ΔΔΔ represents $p < 0.001$

2.3. Rotarod Test Experiment

The experiment was conducted on the 6th, 9th, and 12th days.

Figure 25:
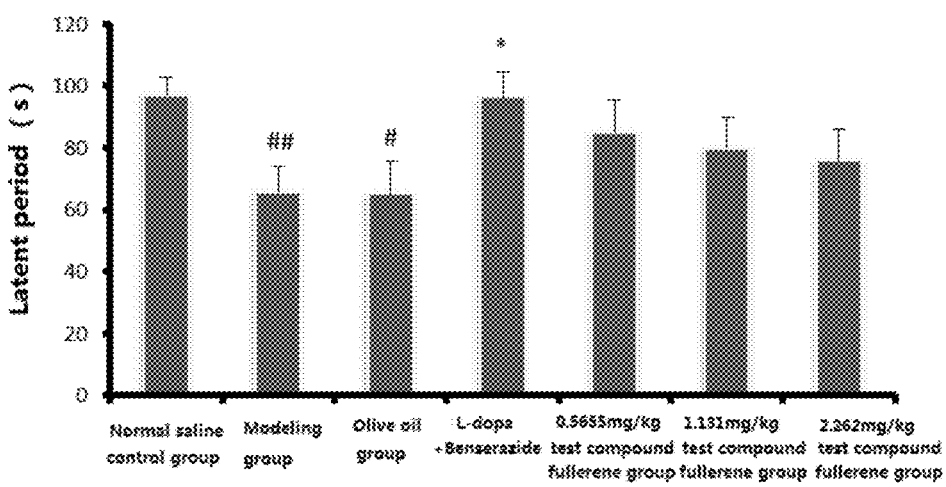
FIG. 25 is a graph showing the results of the motor coordination ability of the mice tested by the rotarod test after the mice administration of day 6 in Example 6.
Figure 26:
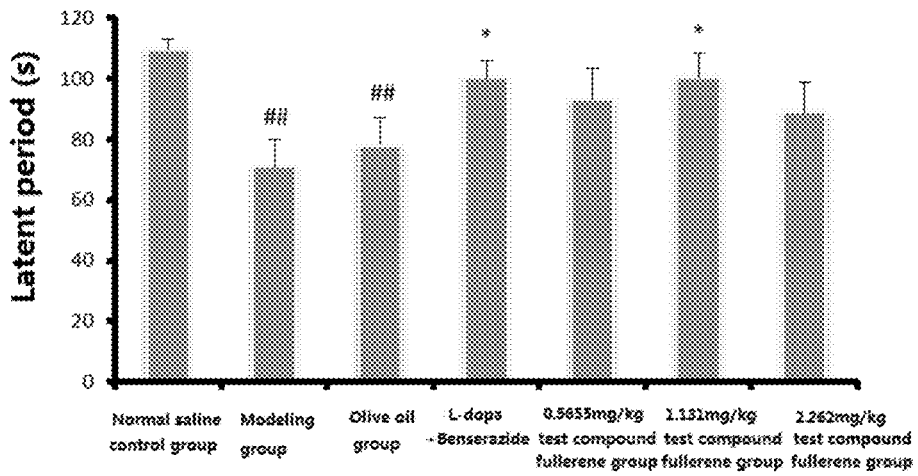
FIG. 26 is a graph showing the results of the motor coordination ability of the mice tested by a rotarod test after the mice administration of day 9 in Example 6.
Figure 27:
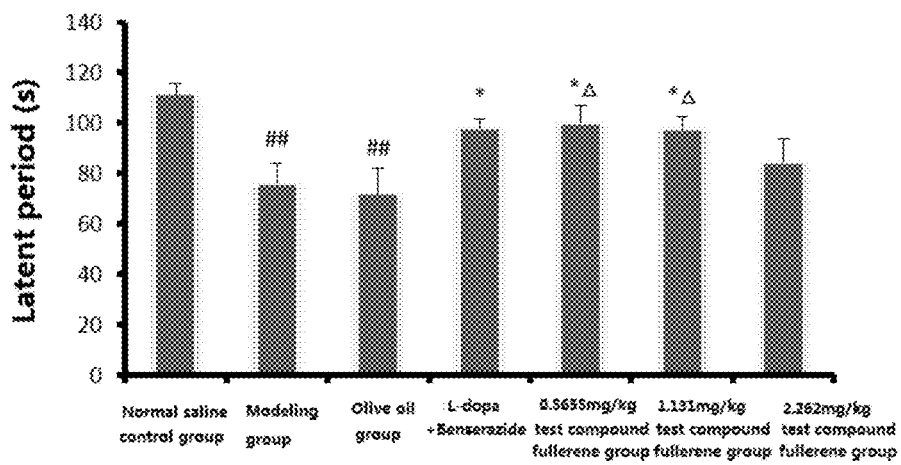
FIG. 27 is a graph showing the results of the motor coordination ability of the mice tested by a rotarod test after the mice administration of day 12 in Example 6.

The mice were subjected to the rotarod test for their motor coordination ability. The results were as shown in Table 7 and FIGS. 25-27. The time taken by the mice in the modeling group and the olive oil group in falling off from the roller for the 1$^{st}$ time (i.e. latent period) was significantly shortened, as compared with the mice in the normal saline control group, there was a significant difference ($p<0.05$-0.01). The latent period of the mice in the modeling group was similar to that of the olive oil group, and there was no statistically significant difference. The latent period of the mice in the positive medicament group and each dose of test compound fullerene group was prolonged more or less as compared to that of the modeling group, and there was a significant difference in the latent period of the mice in 1.131 mg/kg of test compound fullerene group (9th day of the experiment), 0.5655 mg/kg of test compound fullerene group (12th day of the experiment), and 1.131 mg/kg of fullerene (12th day of the experiment) and the positive medicament groups ($p<0.05$) as compared to that of the modeling group. The latent period of the mice fed with fullerenes in each dose of test compound group was prolonged more or less as compared with that of the olive oil group. On the 12th day of experiment, there was a significant difference in 0.5655 mg/kg and 1.131 mg/kg of test compound fullerene groups and olive oil groups. ($p<0.05$). The results showed that fullerenes may significantly relieve MPTP-induced bradykinesia and stiffness in mice and improve animal motor coordination ability.

2. On the 6th, 9th, and 12th days of the experiment, the pole experiment showed that all of the positive medicament group and each dose of test compound fullerene group could significantly improve the motor coordination ability of PD mice, so that the latent period and the down-climbing time were significantly shortened, and there was a statistically significant difference in those of the mice in 2.262 mg/kg of test compound fullerene group. The results showed that fullerenes can significantly relieve MPTP-induced bradykinesia and stiffness in mice and improve PD animal motor coordination ability.

3. On the 6th, 9th, and 12th days of the experiment, the rotarod test showed that falling off from the roller for the 1$^{st}$ time (i.e. the latent period) of the animals in the positive medicament group and each dose of compound test fullerene group (i.e. latent period) was prolonged. As compared with the modeling group, there was a significant difference in the latent period of 1.131 mg/kg of test compound fullerene group (9th day of the experiment), 0.5655 mg/kg of test compound fullerene group (12th day of the experiment), and 1.131 mg/kg of the test compound fullerene group (12th day of the experiment) and the positive medicament group. On the 12th day of the experiment, there was a significant difference in the latent period of 0.5655 mg/kg and 1.131 mg/kg of test compound fullerene groups as compared with that of the olive oil group.

The experimental results showed that fullerene (i.e., $C_{60}$-olive oil) can improve MPTP-induced Parkinson's disease-like symptoms in mice, and there was a certain dose-dependent relationship, and there was no obvious effect of solvent olive oil.

TABLE 7

Effect of fullerene on latent period of rotarod behavior of the model mice suffering from MPTP-induced PD (S)

| Group | Latent peroid (s) 6th day | 9th day | 12th day | Animal number (n) |
|---|---|---|---|---|
| Normal saline control group | 97.20 ± 5.37 | 109.70 ± 3.24 | 111.60 ± 4.13 | 10 |
| Modeling group | 65.61 ± 8.34## | 70.91 ± 9.31## | 76.09 ± 8.03## | 11 |
| Olive oil group | 65.13 ± 10.39# | 77.70 ± 9.61## | 71.97 ± 9.95## | 10 |
| L-dopa + Benserazide | 96.36 ± 7.88* | 100.18 ± 5.65* | 98.09 ± 3.65* | 11 |
| 0.5655 mg/kg test compound fullerene group | 85.10 ± 10.17 | 93.23 ± 10.23 | 99.97 ± 6.98*Δ | 10 |
| 1.131 mg/kg test compound fullerene group | 79.97 ± 9.93 | 100.27 ± 8.15* | 97.57 ± 5.10*Δ | 10 |
| 2.262 mg/kg test compound fullerene group | 76.03 ± 9.91 | 88.93 ± 9.89 | 84.47 ± 9.37 | 10 |

As compared with normal saline control group,
represents $p < 0.05$,
represents $p < 0.01$;
as compared with modeling group,
*represents $p < 0.05$;
as compared with olive oil group,
Δrepresents $p < 0.05$,

IV. Summary of the Experiments

MPTP was injected subcutaneously for the whole 5 days for modeling, and the normal saline or olive oil or fullerene was given while modeling. Thereafter, the administration of the normal saline or olive oil or fullerene was continued for 7 days, and 12 days in all. The mice were performed behavioral evaluation on the 5th, the 6th, the 9th, and the 12th days of the administration. The results showed that:

1. On the 5th day of experiment, the total activity time, activity distance and vertical activity time of the mice in each dose of test compound fullerene group were higher than those in the olive oil group, of which 2.262 mg/kg of test compound fullerene group was the most significant.

What is claimed is:

1. A method of treating Parkinson's disease, comprising the step of: administering an effective dose of an oil-soluble metallofullerene to a subject in need of treatment for Parkinson's disease, wherein the oil-soluble metallofullerene comprises an oil-soluble Gd@$C_{82}$;
    wherein the treating Parkinson's disease includes treating limbs tremor, rigid limbs, hypokinesia, bradykinesia, or discordant movement caused by Parkinson's disease.

2. The method according to claim 1, wherein the oil-soluble metallofullerene is obtained through oil-soluble modification of a Gd@$C_{82}$, and the oil-soluble modification method comprises coating the Gd@$C_{82}$ with an oil solution.

3. The method according to claim 2, wherein the oil solution is a single ingredient oil or a mixture of different oils, and the oil is vegetable oil or animal fat.

4. The method according to claim 2, wherein the oil-soluble modification is to disperse a $Gd@C_{82}$ in the oil solution to obtain an oil-soluble modified liquid; the optional means of dispersion is ball milling or ultrasonication of the mixture of the $Gd@C_{82}$ and the oil solution, followed by centrifugation to remove precipitate, and filtration of resulting supernatant.

5. The method according to claim 4, wherein the concentrations of the oil-soluble metallofullerene in the oil-soluble modified liquid are from 0.01 to 100 mg/mL, from 0.01 to 10 mg/mL, from 10 to 20 mg/mL, from 20 to 30 mg/mL, from 30 to 40 mg/mL, from 0.01 mg/mL to 0.8 mg/mL, or from 0.4 to 0.8 mg/mL.

6. The method according to claim 1, wherein the oil-soluble metallofullerene is applied at a dose of from 0.01 mg/kg/d to 1000 mg/kg/d, from 1 to 100 mg/kg/d, from 10 mg/kg/d to 100 mg/kg/d, from 1 to 20 mg/kg/d, from 0.1 to 10 mg/kg/d, 4 mg/kg/d or from 0.5655 mg/kg/d to 2.262 mg/kg/d.

7. The method according to claim 1, wherein the subject is a human, a mouse, a guinea pig, a rat, a dog, a rabbit, or a monkey.

8. The method according to claim 1, wherein the oil-soluble metallofullerene comprises $Gd@C_{82}$ coated with olive oil.

9. The method according to claim 1, wherein the oil-soluble metallofullerene is administered orally, by injection or intraperitoneally.

10. The method according to claim 3, wherein the oil is selected from olive oil, linseed oil, sunflower oil, corn germ oil, soybean oil, or squalane.

* * * * *